(12) United States Patent
Froman et al.

(10) Patent No.: US 8,999,411 B2
(45) Date of Patent: Apr. 7, 2015

(54) SOYBEAN PLANT AND SEED CORRESPONDING TO TRANSGENIC EVENT MON87769 AND METHODS FOR DETECTION THEREOF

(71) Applicant: Monsanto Technology LLC, St. Louis, MO (US)

(72) Inventors: Byron Froman, Davis, CA (US); Can Duong, St. Louis, MO (US); Jennifer Listello, O'Fallon, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 14/179,524

(22) Filed: Feb. 12, 2014

(65) Prior Publication Data

US 2014/0256971 A1    Sep. 11, 2014

Related U.S. Application Data

(62) Division of application No. 12/865,844, filed as application No. PCT/US2009/033930 on Feb. 12, 2009, now Pat. No. 8,692,076.

(60) Provisional application No. 61/055,401, filed on May 22, 2008, provisional application No. 61/029,197, filed on Feb. 15, 2008.

(51) Int. Cl.
*C11B 1/00* (2006.01)
*C10M 169/00* (2006.01)
*A01H 5/10* (2006.01)
*C11B 1/10* (2006.01)
*C12N 15/82* (2006.01)
*C12Q 1/68* (2006.01)

(52) U.S. Cl.
CPC .............. *C11B 1/10* (2013.01); *C12N 15/8247* (2013.01); *C12Q 1/6895* (2013.01)

(58) Field of Classification Search
None
See application file for complete search history.

(56) References Cited

U.S. PATENT DOCUMENTS

| | | | |
|---|---|---|---|
| 5,888,947 A * | 3/1999 | Lambert et al. ............ | 508/491 |
| 7,622,632 B2 | 11/2009 | Ursin et al. | |
| 8,501,407 B2 | 8/2013 | Brinker et al. | |
| 2006/0156435 A1 | 7/2006 | Ursin et al. | |
| 2008/0063691 A1 | 3/2008 | Ursin et al. | |
| 2011/0302667 A1 | 12/2011 | Brown et al. | |
| 2014/0041075 A1 | 2/2014 | Brinker et al. | |
| 2014/0373190 A1 | 12/2014 | Brown et al. | |

FOREIGN PATENT DOCUMENTS

| | | |
|---|---|---|
| CN | 1871353 A | 11/2006 |
| WO | WO 02/34946 A2 | 5/2002 |
| WO | WO 2005/021761 A1 | 3/2005 |

OTHER PUBLICATIONS

Hohe et al 2003 (Plant Cell Reports 21:1135-1142).*
U.S. Appl. No. 13/945,741, filed Jul. 18, 2013, Brinker et al.
Eckert et al., "Co-expression of the borage delta-6 desaturase and the arabidopsis delta-15 desaturase results in high accumulation of stearidonic acid in the seeds of transgenic soybean," *Planta*, 224(5): 1050-1057,2006.
Taverniers et al., "Event-specific plasmid standards and real-time PCR methods for transgenic Bt11, Bt176, and GA21 maize and transgenic GT73 canola," *Agri. Food Chem.*, 53:3041-3052, 2005.
Weising et al., "Foreign genes in plants: transfer, structure, expression, and applications," *Annu. Rev. Genet.*, 22:421-477, 1988.
New England BioLabs Inc. 1998/99 Catalog, (NEB Catalog), pp. 121 and 284, undated.
Final Office Action regarding U.S. Appl. No. 11/801,114, dated Aug. 26, 2009.
Anklam et al., "Analytical methods for detection and determination of genetically modified organisms in agricultural crops and plant-derived food products", *Eur. Food Res. Technol.* 214:3-26,2002.
English translation of Office Action issued Nov. 22, 2011, in Chinese Patent Application No. 200980104350.X.
Alignment of SEQ. ID Nos. 2 and 6 from U.S. Appl. No. 12/865,844 and SEQ ID Nos. 2 and 8 from U.S. Appl. No. 13/151,082 undated.
Alignment of SEQ ID No. 1 from U.S. Appl. No. 12/865,844 and SEQ ID Nos. 1 and 7 from U.S. Appl. No. 13/945,741, undated.
Genbank Accession No. BX891430, Oct. 10, 2003.
Opperman et al. Genbank accession # ET721878, 2009.
Hohe et al. 2003 *Plant Cell Reports* 21 :1135-1142.
Koukalova et al. *Theor. and App. Genet.* 78:77-80, 1989.
Rosso et al. *Plant Molecular Biology* 53:1-2, 247-259, 2003.
Desai et al. Genbank accession # EE878000, 2006.
Staswick et al. *Plant Physiology* 127:1819-1826, Dec. 2001.
The Qiagen Taq PCR Core Kit product page. Undated.
Quack et al., *America Journal of Human Genetics*, 65:1268-1278, 1999.
Town et al., Genbank accession # AC207600, 2007.
U.S. Appl. No. 14/333,479, filed Jul. 16, 2014, Brown et al.
USPTO: Notice of Allowance for U.S. Appl. No. 13/151,082, issued Jun. 17, 2014.

* cited by examiner

*Primary Examiner* — Eileen B O Hara
*Assistant Examiner* — Matthew Keogh
(74) *Attorney, Agent, or Firm* — Dentons US LLP; Byron V. Olsen, Esq.

(57) ABSTRACT

The present invention provides transgenic soybean event MON87769, and cells, seeds, and plants comprising DNA diagnostic for the soybean event. The invention also provides compositions comprising nucleotide sequences that are diagnostic for said soybean event in a sample, methods for detecting the presence of said soybean event nucleotide sequences in a sample, probes and primers for use in detecting nucleotide sequences that are diagnostic for the presence of said soybean event in a sample, growing the seeds of such soybean event into soybean plants, and breeding to produce soybean plants comprising DNA diagnostic for the soybean event.

2 Claims, 2 Drawing Sheets

SOYBEAN PLANT AND SEED CORRESPONDING TO TRANSGENIC EVENT MON87769 AND METHODS FOR DETECTION THEREOF

CROSS REFERENCE TO RELATED APPLICATIONS

This application is a divisional of U.S. patent application Ser. No. 12/865,844, filed Nov. 9, 2010, which is a 371 National Stage application of International Application No. PCT/US2009/033930, filed Feb. 12, 2009, which claims the priority of U.S. Provisional Applications, Ser. No. 61/029,197 filed Feb. 15, 2008, and Ser. No. 61/055,401 filed May 22, 2008, the entire disclosures of which are incorporated herein by reference.

INCORPORATION-BY-REFERENCE OF SEQUENCE LISTING IN COMPUTER READABLE FORM

The Sequence Listing, which is a part of the present disclosure, includes a computer readable form 37 KB file entitled "MONS193WO_ST25.txt" comprising nucleotide sequences of the present invention. The subject matter of the Sequence Listing is incorporated herein by reference in its entirety.

BACKGROUND OF THE INVENTION

1. Field of the Invention

The present invention relates to transgenic soybean plants comprising event MON87769, progeny plants, and seed thereof. The event exhibits an oil composition comprising stearidonic acid. The invention also relates to methods for detecting the presence of said soybean event in a biological sample, and provides nucleotide sequences that are unique to the event.

2. Description of Related Art

Soybean is an important crop and is a primary food source in many areas of the world. The methods of biotechnology have been applied to soybean for improvement of agronomic traits and the quality of the product. One such quality trait is a soybean oil comprising stearidonic acid (SDA).

It would be advantageous to be able to detect the presence of transgene/genomic DNA of a particular plant in order to determine whether progeny of a sexual cross contain the transgene/genomic DNA of interest. In addition, a method for detecting a particular plant would be helpful when complying with regulations requiring the pre-market approval and labeling of foods derived from the recombinant crop plants.

The polyunsaturated fatty acids (PUFAs) are known to provide health benefits when consumed. An oil containing SDA, a PUFA, would be advantageous as part of a healthy diet in humans and other animals. SDA may be sourced from plant and animal sources. Commercial sources of SDA include the plant genera *Trichodesma, Borago* (borage) and *Echium* as well as fish. However, there are several disadvantages associated with commercial production of PUFAs from natural sources. Natural sources of PUFAs, such as animals and plants, tend to have highly heterogeneous oil compositions. The oils obtained from these sources therefore can require extensive purification to separate out one or more desired PUFAs or to produce an oil which is enriched in one or more PUFAs. Natural sources of PUFAs also are subject to uncontrollable fluctuations in availability. Fish stocks may undergo natural variation or may be depleted by over fishing. Fish oils also have unpleasant tastes and odors, which may be impossible to economically separate from the desired product and can render such products unacceptable as food supplements. Animal oils, and particularly fish oils, can accumulate environmental pollutants. Foods may be enriched with fish oils, but again, such enrichment is problematic because of cost and declining fish stocks worldwide. Nonetheless, if the health messages to increase fish intake were embraced by communities, there would likely be a problem in meeting demand for fish. Furthermore, there are problems with sustainability of this industry, which relies heavily on wild fish stocks for aquaculture feed (Naylor et al., *Nature* 405:1017-1024, 2000).

Therefore, it would be advantageous to produce a PUFA such as SDA in a land-based terrestrial crop plant system, which can be manipulated to provide production of commercial quantities of SDA. In commercial oilseed crops, such as canola, soybean, corn, sunflower, safflower, or flax, the conversion of some fraction of the mono and polyunsaturated fatty acids that typify their seed oil to SDA requires the seed-specific expression of the enzymes delta 6-desaturase and delta 15-desaturase. Oils derived from plants expressing elevated levels of Δ6- and Δ15-desaturases are rich in SDA. As there is also a need to increase omega-3 fatty acid intake in humans and animals, there is a need to provide a wide range of omega-3 enriched foods and food supplements so that subjects can choose feed, feed ingredients, food and food ingredients which suit their usual dietary habits. It is also advantageous to provide commercial quantities of SDA in a soy plant.

The expression of foreign genes in plants is known to be influenced by their chromosomal position, perhaps due to chromatin structure (e.g., heterochromatin) or the proximity of transcriptional regulation elements (e.g., enhancers) close to the integration site Weising et al. (*Ann. Rev. Genet* 22:421-477, 1988). For this reason, it is often necessary to screen a large number of events in order to identify an event characterized by optimal expression of an introduced gene of interest. For example, it has been observed in plants and in other organisms that there may be wide variation in the levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce several hundreds to several thousands different events and screen the events for a single event that has the desired transgene expression levels and patterns for commercial purposes. An event that has the desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are suitably adapted to specific local growing conditions.

It is possible to detect the presence of a transgene by any well known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be event-specific (e.g. useful for discriminating between different events), particularly those produced using the same DNA construct, unless the sequence of chromosomal DNA adjacent to the inserted DNA ("flanking DNA") is known. An event-specific PCR assay is discussed, for example, by Taverniers et al. (*J. Agric. Food Chem.*, 53: 3041-3052, 2005) in which an event-specific tracing system for transgenic maize lines Bt11, Bt176, and GA21 and for canola event GT73 is demonstrated. In this study, event-specific primers and probes were designed based upon the sequences of the genome transgene junctions for each event. Event-specific detection methods may also be required by regulatory agencies charged with approving the use of transgenic plants comprising a given transformation event. Transgenic plant event specific DNA detection methods have also been described in U.S. Pat. Nos. 6,893,826; 6,825,400; 6,740,488; 6,733,974; 6,689,880; 6,900,014 and 6,818,807.

SUMMARY OF THE INVENTION

The present invention is related to soybean plants comprising the transgenic soybean event designated MON87769 and progeny that are indistinguishable from soybean event MON87769 (to the extent that such progeny also contain at least one allele that corresponds to the inserted transgenic DNA) thereof. Another aspect of the invention is (are) progeny plants, or seeds, or regenerable parts of the soybean plants and seeds, comprising the soybean event MON87769. The invention also includes parts of plants comprising soybean event MON87769 that include, but are not limited to pollen, ovule, flowers, shoots, roots, stems, leaves, pods, seeds and meristematic tissues. Novel genetic compositions contained in the genome of plants comprising MON87769 and products from plants comprising MON87769, such as oil, meal, flour, food products, protein supplements and biomasses remaining in a field from which soybean plants corresponding to MON87769 have been harvested are aspects of this invention.

The invention provides a soybean plant with an oil composition comprising SDA that has all of the physiological and morphological characteristics of a soybean plant comprising event MON87769.

According to one aspect of the invention, compositions and methods are provided for detecting the presence of the transgene/genomic insertion region from a novel soybean plant comprising SEQ ID NO:1 and/or SEQ ID NO:2, or the event designated MON87769, wherein a sample of seed comprising soybean event MON87769 is deposited under ATCC Accession No. PTA-8911. DNA sequences are provided that comprise at least one junction sequence of event MON87769 selected from the group consisting of SEQ ID NO: 1 ("[A] SEQ ID NO:1" corresponding to positions 979 through 998 of "[F] SEQ ID NO: 6" as shown in FIG. 2) and SEQ ID NO: 2 ("[B] SEQ ID NO:2" corresponding to positions 8345 through 8365 of "[F] SEQ ID NO: 6", as shown in FIG. 2) and complements thereof; wherein a junction sequence is a nucleotide sequence that spans the point at which heterologous DNA inserted into the genome is linked to the soybean cell genomic DNA and detection of this sequence in a biological sample containing soybean DNA is diagnostic for the presence of the soy event MON87769 DNA in said sample. Such junction sequences contain at least SEQ ID NO: 1 and/or SEQ ID NO: 2 and/or the complements thereof. A soybean event MON87769 and soybean seed comprising these DNA molecules is an aspect of this invention.

DNA sequences that comprise a novel transgene/genomic insertion region, SEQ ID NO: 3 [C], SEQ ID NO: 4 [D] and SEQ ID NO: 5 [E] or SEQ ID NO: 1 [A], SEQ ID NO: 2 [B] and SEQ ID NO: 5 [E] (also referring to FIG. 2) from soybean event MON87769 are aspects of this invention. The soybean plant and seed comprising these molecules are also aspects of this invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO: 3 or SEQ ID NO: 5 and a DNA molecule of similar length of any portion of a 5' flanking soybean genomic DNA region of SEQ ID NO: 3, where these DNA molecules when used together are useful as DNA primers in a DNA amplification method that produces an amplicon. The amplicon produced using these DNA primers in the DNA amplification method is diagnostic for soybean event MON87769 when the amplicon contains SEQ ID NO: 1. Any amplicon produced by DNA primers homologous or complementary to any portion of SEQ ID NO: 3 and SEQ ID NO: 5, and any amplicon that comprises SEQ ID NO: 1 is an aspect of the invention.

According to another aspect of the invention, two DNA molecules are provided for use in a DNA detection method, wherein the first DNA molecule comprises at least 11 or more contiguous polynucleotides of any portion of the transgene region of the DNA molecule of SEQ ID NO: 4 or SEQ ID NO: 5 and a DNA molecule of similar length of any portion of a 3' flanking soybean genomic DNA of SEQ ID NO: 4, where these DNA molecules are useful as DNA primers in a DNA amplification method. The amplicon produced using these DNA primers in the DNA amplification method is diagnostic for soybean event MON87769 when the amplicon contains SEQ ID NO: 2. Any amplicons produced by DNA primers homologous or complementary to any portion of SEQ ID NO: 4 and SEQ ID NO: 5, and any amplicon that comprises SEQ ID NO: 2 is an aspect of the invention.

According to another aspect of the invention, methods of detecting the presence of DNA corresponding to the soybean event MON87769 in a sample are provided. Such methods comprise: (a) contacting the sample comprising DNA with a primer set that, when used in a nucleic acid amplification reaction with genomic DNA from soybean event MON87769, produces an amplicon that is diagnostic for soybean event MON87769; (b) performing a nucleic acid amplification reaction, thereby producing the amplicon; and (c) detecting the amplicon wherein said amplicon comprises SEQ ID NO: 1 and/or SEQ ID NO: 2.

Another aspect of the invention is a soybean plant, or seed, or product derived from the plant or seed, comprising event MON87769 wherein the genomic DNA comprises a DNA molecule consisting essentially of the nucleotide sequence of SEQ ID NO: 3 from about positions 1 to 988, the nucleotide sequence of SEQ ID NO: 5 from about positions 1 to 7367 and the nucleotide sequence of SEQ ID NO: 4 from about positions 1 to 939 (the contig of which is presented as SEQ ID NO: 6), and complements thereof. A sample of seed comprising soybean event MON87769 has been deposited under ATCC Accession No. PTA-8911. A soybean plant, or seed, or product derived from the plant or seed comprising event MON87769, in which the genomic DNA when isolated from the soybean plant, or seed, or product comprises a DNA molecule incorporating SEQ ID NO: 1 and/or SEQ ID NO: 2, and complements thereof, is also an aspect of the invention.

A further aspect of the invention is a soybean plant, or seed, or product derived from the plant or seed comprising event MON87769 wherein the genomic DNA comprises a DNA molecule consisting essentially of the nucleotide sequence of SEQ ID NO: 6 from about positions 1 to 9294 and complements thereof. A soybean plant, or seed, or product derived from the plant or seed, in which the genomic DNA when isolated from the soybean plant, or seed, or product, comprises a DNA molecule incorporating SEQ ID NO: 1 and/or SEQ ID NO: 2, and complements thereof, is also provided.

Another aspect of the invention is a soybean plant, or seed, or product derived from the plant or seed of MON87769, in which the genomic DNA when isolated from the soybean plant, or seed, or product produces an amplicon in a DNA amplification method, wherein said amplicon comprises SEQ ID NO: 1 and/or SEQ ID NO: 2.

According to another aspect of the invention, methods of detecting the presence of a DNA corresponding to the MON87769 event in a sample, such methods comprising: (a) contacting the sample comprising DNA with a probe that hybridizes under stringent hybridization conditions with genomic DNA from soybean event MON87769 and does not hybridize under the stringent hybridization conditions with a control soybean plant; (b) subjecting the sample and probe to stringent hybridization conditions; and (c) detecting hybridization of the probe to the soybean event MON87769 DNA wherein said probe is selected from the group consisting of SEQ ID NO:1 and/or SEQ ID NO:2.

Another aspect of the invention is a method of determining zygosity of the progeny of soybean event MON87769, the method comprising (a) contacting the sample comprising soybean DNA with the primer set SQ5923 (SEQ ID NO: 8), SQ5924 (SEQ ID NO: 9), SQ5925 (SEQ ID NO: 11), and the probe set 6FAM™-labeled PB2511 (SEQ ID NO: 10) and VIC™-labeled PB2512 (SEQ ID NO: 12) that when used in a nucleic-acid amplification reaction with genomic DNA from a plant comprising soybean event MON87769, produces a first amplicon, releasing a fluorescent signal from the combination of primers SQ5923 and SQ5924 and a 6FAM™-labeled primer/probe, PB2511 that is diagnostic for soybean event MON87769 (b) performing a nucleic acid amplification reaction, thereby producing the first amplicon; and (c) detecting said first amplicon; and (d) contacting the sample comprising soybean DNA with the primer set, SQ59224 and SQ5925 and a VIC™-labeled probe, PB2512 that when used in a nucleic-acid amplification reaction with genomic DNA from soybean plants produces a second amplicon, releasing a fluorescent signal that is diagnostic of the wild-type soybean genomic DNA homologous to the soybean genomic region of a transgene insertion identified as soybean event MON87769; (e) performing a nucleic acid amplification reaction, thereby producing the second amplicon and (f) detecting said second amplicon; and (g) comparing the first and second amplicons in a sample, wherein the presence of both amplicons indicates the sample is heterozygous for the transgene insertion.

Another aspect of the invention is a method of determining zygosity of the progeny of a plant comprising soybean event MON87769, the method comprising (a) contacting the sample comprising soybean DNA with the primer set SQ5923 (SEQ ID NO: 8), SQ5924 (SEQ ID NO: 9), and SQ5925 (SEQ ID NO: 11), that when used in a nucleic-acid amplification reaction with genomic DNA from soybean event MON87769, produces a first amplicon from the combination of primers SQ5923 and SQ5924 that is diagnostic for soybean event MON87769 (b) performing a nucleic acid amplification reaction, thereby producing the first amplicon; and (c) detecting said first amplicon; and (d) contacting the sample comprising soybean DNA with the primer set, SQ5924 and SQ5925 that when used in a nucleic-acid amplification reaction with genomic DNA from soybean plants produces a second amplicon from the combination of primers SQ5924 and SQ5925 that is diagnostic of the wild-type soybean genomic DNA homologous to the soybean genomic region of a transgene insertion identified as soybean event MON87769; (e) performing a nucleic acid amplification reaction, thereby producing the second amplicon and (0 detecting said second amplicon; and (g) comparing the first and second amplicons in a sample, wherein the presence of both amplicons indicates the sample is heterozygous for the transgene insertion.

Kits for the detection of soybean event MON87769 are provided which use primers designed from SEQ ID NO: 3, SEQ ID NO: 4 and SEQ ID NO: 5. An amplicon produced using said kit is diagnostic for MON87769 when the amplicon (1) contains either nucleotide sequences set forth as SEQ ID NO: 1 or SEQ ID NO: 2 or (2) contains both SEQ ID NO: 1 and SEQ ID NO: 2.

Another aspect of the invention is a soybean plant, or seed, or seed progeny, or product derived from the plant or seed of a plant comprising event MON87769. In certain embodiments, a method for producing a soybean plant comprising altered PUFA content, comprising introgressing soybean event MON87769 into a soybean plant genome, wherein a sample of seed comprising transformation event MON87769 has been deposited under ATCC Accession No. PTA-8911, is also provided.

Seed for sale for planting or for making commodity products is an aspect of the invention. Such commodity products include, but are not limited to, whole or processed soy seeds, animal feed, vegetable oil, meal, flour, nontoxic plastics, printing inks, lubricants, waxes, hydraulic fluids, electric transformer fluids, solvents, cosmetics, hair care products, soymilk, soy nut butter, natto, tempeh, soy protein concentrate, soy protein isolates, texturized soy protein concentrate, hydrolyzed soy protein, whipped topping, cooking oil, salad oil, shortening, lecithin, edible whole soybeans (raw, roasted, or as edamamé), soymilk, soy yogurt, soy cheese, tofu, yuba and biodiesel.

The foregoing and other aspects of the invention will become more apparent from the following detailed description.

BRIEF DESCRIPTION OF THE SEQUENCES

Figure 1:
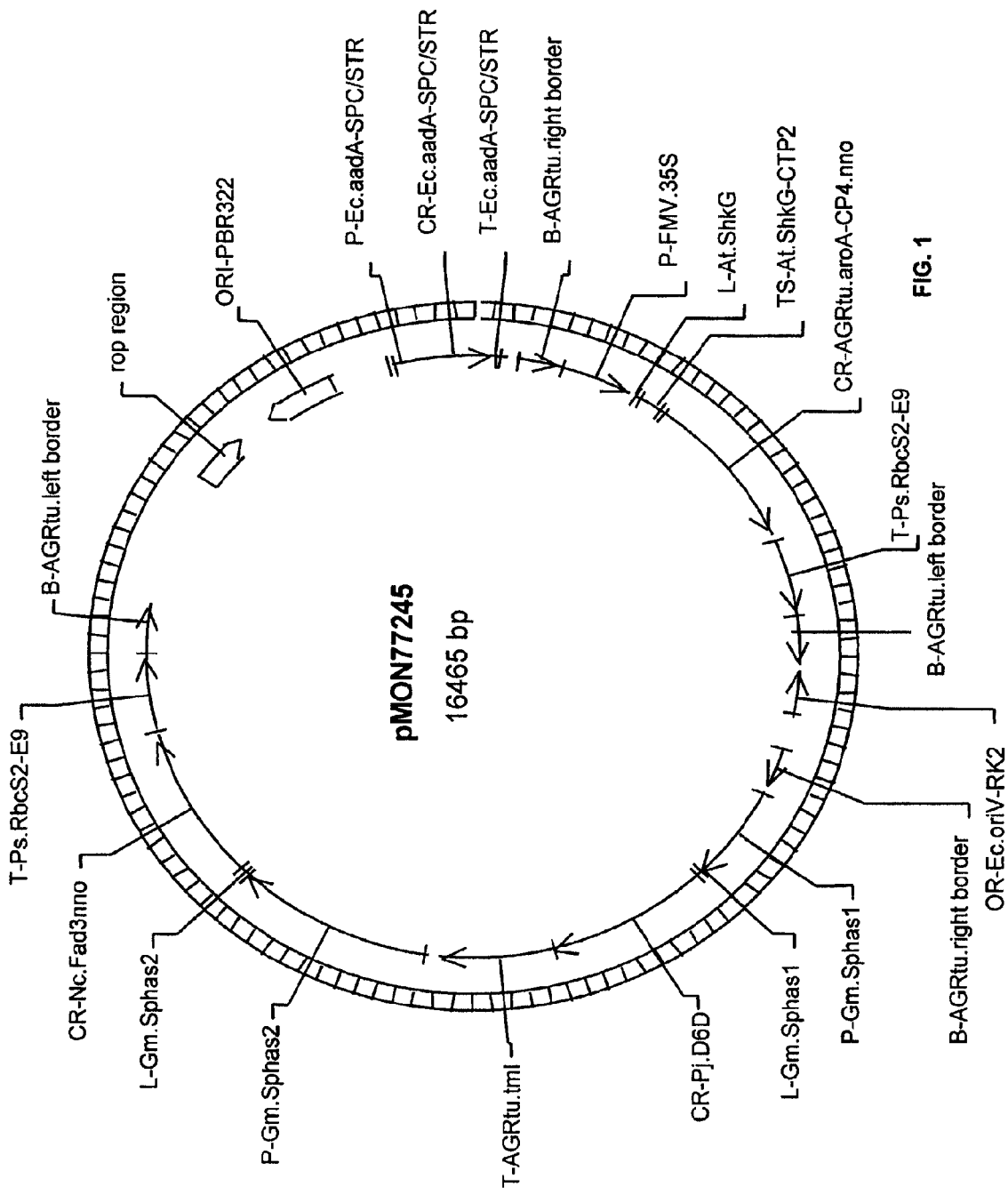
FIG. 1. Map of binary transformation vector, pMON77245, that was used to generate a soybean plant comprising event MON87769.

SEQ ID NO: 1—A 20 nucleotide sequence representing the right border junction between the soybean genomic DNA and the integrated expression cassette. This sequence corresponds to positions 979 to 998 of SEQ ID NO: 6. In addition, SEQ ID NO: 1 ([A] of FIG. 2) is a nucleotide sequence corresponding to positions 979 through 988 of SEQ ID NO: 3 ([C], see FIG. 2) and the integrated right border of the desaturase expression cassette corresponding to positions 1 through 10 of SEQ ID NO: 5 ([E], see FIG. 2).

SEQ ID NO: 2—A 20 nucleotide sequence representing the left border junction between the integrated expression cassette and the soybean genomic DNA. This sequence corresponds to positions 8346 to 8365 of SEQ ID NO: 6. In addition, SEQ ID NO: 2 ([B], see FIG. 2) is a nucleotide sequence corresponding positions 7358 through 7367 SEQ ID NO: 5 ([E], see FIG. 2) and the 3' flanking sequence corresponding to positions 1 through 10 of SEQ ID NO: 4 ([D], see FIG. 2).

SEQ ID NO: 3—The 5' sequence flanking the inserted DNA of MON87769 up to and including a region of T-DNA insertion.

SEQ ID NO: 4—The 3' sequence flanking the inserted DNA of MON87769 up to and including a region of T-DNA insertion.

SEQ ID NO: 5—The sequence of the integrated desaturase expression cassette, including right and left border sequence after integration.

SEQ ID NO: 6—A 9294 bp nucleotide sequence representing the contig of the 5' sequence flanking the inserted DNA of MON87769 (SEQ ID NO: 3), the sequence of the integrated expression cassette (SEQ ID NO: 5) and the 3' sequence flanking the inserted DNA of MON87769 (SEQ ID NO: 4).

SEQ ID NO: 7—The desaturase expression cassette of pMON77245.

SEQ ID NO: 8—Primer SQ5923 used to identify MON87769 events as well as the zygosity of MON87769 events. Primer SQ5923 corresponds to a region 5' flanking the inserted desaturase cassette close to the right T-DNA insertion border corresponding to positions 944 to 968 of SEQ ID NO: 6. A PCR amplicon using the combination of primers SQ5923 and SQ5924 is positive for the presence of the event MON87769.

SEQ ID NO: 9—Primer SQ5924 used to identify MON87769 events as well as the zygosity of MON87769 events. Primer SQ5924 is complimentary to the 5' region of the inserted desaturase cassette, close to the right T-DNA insertion border corresponding to positions 1007 to 1025 of SEQ ID NO: 6. A PCR amplicon using the combination of primers SQ5923 and SQ5924 is positive for the presence of the event MON87769.

SEQ ID NO: 10—Probe PB2511 used to identify MON87769 events. This probe is a 6FAM™-labeled synthetic oligonucleotide whose sequence corresponds to positions 986 to 1005 of SEQ ID NO: 6. Release of a fluorescent signal in an amplification reaction using primers SQ5923 and SQ5924 in combination with 6FAM™-labeled probe PB2511 is diagnostic of event MON87769.

SEQ ID NO: 11—Primer SQ5925 used to determine zygosity of MON87769 events. Primer SQ5925 is complimentary to the 3' region flanking the inserted expression cassette, close to the left T-DNA corresponding to positions 8372 to 8395 of SEQ ID of SEQ ID NO: 6. Detection of a PCR amplicon using 6FAM™-labeled Probe PB2512 and primers SQ5923 and SQ5925 is positive for presence of wild type in a zygosity assay.

SEQ ID NO: 12—Probe PB2512 used to determine zygosity of MON87769 events. This probe is a VIC™-labeled synthetic oligonucleotide whose sequence corresponds to a region of the wild-type genomic DNA, immediately following the region of homology to primer SQ5925 at the point of insertion of the expression cassette for event MON87769. A PCR amplicon produced using primers SQ5924 and SQ5925 causes the release of a fluorescent signal using probe PB 1112 which is positive for the presence of the wild-type allele in a zygosity assay for event MON87769.

DETAILED DESCRIPTION OF THE PREFERRED EMBODIMENTS

This invention relates to a transgenic soybean (*Glycine max*) plant comprising event MON87769 with an oil composition comprising stearidonic acid (SDA) and seed and progeny thereof. The invention further relates to the DNA construct inserted to soybean event MON87769, the transgene/genomic insertion region found in soybean plants or seeds comprising event MON87769, and the detection of the transgene/genomic insertion region in soybean plants or seed comprising event MON87769, and progeny thereof.

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994.

As used herein, the term "soybean" means *Glycine max* and includes all plant varieties that can be bred with soybean, including wild soybean species as well as those plants belonging to *Glycine soja* that permit breeding between species.

As used herein, the term "comprising" means "including but not limited to".

"Glyphosate" refers to N-phosphonomethylglycine and its salts. N-phosphonomethylglycine is a well-known herbicide that has activity on a broad spectrum of plant species.

"Desaturase" refers to a polypeptide that can desaturate or catalyze formation of a double bond between consecutive carbons of one or more fatty acids to produce a mono- or poly-unsaturated fatty acid or a precursor thereof. Of particular interest are polypeptides that can catalyze the conversion of OA to LA, LA to ALA, or ALA to SDA, which includes enzymes which desaturate at the 12, 15, or 6 positions. Considerations for choosing a specific polypeptide having desaturase activity include, but are not limited to, the pH optimum of the polypeptide, whether the polypeptide is a rate limiting enzyme or a component thereof, whether the desaturase used is essential for synthesis of a desired PUFA, and/or whether a co-factor is required by the polypeptide. The expressed polypeptide preferably has characteristics that are compatible with the biochemical environment of its location in the host cell. For example, the polypeptide may have to compete for substrate(s).

A "commodity product" refers to any product which is comprised of material derived from soybean or soybean oil and is sold to consumers. Processed soybeans are the largest source of protein feed and vegetable oil in the world. The soybean plant MON87769 can be used to manufacture commodities typically acquired from soy. A sample of seed comprising soybean event MON87769 is deposited under ATCC Accession No. PTA-8911, as noted below. Soybeans of MON87769 can be processed into meal, flour, or oil as well as be used as a protein or oil source in animal feeds for both terrestrial and aquatic animals. Soybeans and soybean oils from plants, plant parts, or seeds that comprise event MON87769 can be used in the manufacture of many different products, not limited to, nontoxic plastics, printing inks, lubricants, waxes, hydraulic fluids, electric transformer fluids, solvents, cosmetics, and hair care products. Soybeans and oils from plants, plant parts, or seeds that comprise event pMON87769 can be suitable for use in a variety of soyfoods made from whole soybeans, such as soymilk, soy nut butter, natto, and tempeh, and soyfoods made from processed soybeans and soybean oil, including soybean meal, soy flour, soy protein concentrate, soy protein isolates, texturized soy protein concentrate, hydrolyzed soy protein, whipped topping, cooking oil, salad oil, shortening, and lecithin. Whole soybeans are also edible, and are typically sold to consumers raw, roasted, or as edamamé. Soymilk, which is typically produced by soaking and grinding whole soybeans, may be consumed without other processing, spray-dried, or processed to form soy yogurt, soy cheese, tofu, or yuba.

Oils of MON87769 can be used to make biodiesel. The use of biodiesel in conventional diesel engines results in substantial reductions of pollutants such as sulfates, carbon monoxide, and particulates compared to petroleum diesel fuel, and use in school buses can greatly reduce exposure to toxic diesel exhaust. Biodiesel is typically obtained by extracting, filtering and refining soybean oil to remove free fats and phospholipids, and then trans-esterifying the oil with methanol to form methyl esters of the fatty acids (see for example U.S. Pat. No. 5,891,203). The resultant soy methyl esters are commonly referred to as "biodiesel." The oil derived from plants, plant parts, or seeds that comprise event MON87769 may also be used as a diesel fuel without the formation of methyl esters, such as, for example, by mixing acetals with the oil (see for example U.S. Pat. No. 6,013,114). The seeds of plants, plant parts, or seeds that comprise event MON87769 used to make said oils can be identified by the methods of the present invention. It is expected that purified oil from MON87769 event seeds or mixtures of seeds some or all of which are MON87769 will have relatively little or no DNA available for testing. However, the seeds from which the oils are extracted can be characterized with the method of the present invention to identify the presence of the MON87769 event within the population of seeds used to make said oils. Also, plant waste from the process used to make said oils can be used in the methods of the present invention to identify the presence of plants, plant parts, or seeds comprising the MON87769 event within a mixture of plants or seeds processed to make said oils. Likewise, plant debris left after making a commodity product, or left behind following harvest of the soybean seed, can be characterized by the methods of the present invention to identify MON87769 events within the raw materials used to make said commodity products.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA. The present invention relates to DNA sequences unique to or diagnostic for event MON87769, and plant cells, tissues, seeds and processed products derived from plant tissues comprising event MON87769.

As used herein when referring to an "isolated DNA molecule", it is intended that the DNA molecule be one that is present, alone or in combination with other compositions, but not within its natural environment. For example, a coding sequence, intron sequence, untranslated leader sequence, promoter sequence, transcriptional termination sequence, and the like, that are naturally found within the DNA of a soybean genome are not considered to be isolated from the soybean genome so long as they are within the soybean genome. However, each of these components, and subparts of these components, would be "isolated" within the scope of this disclosure so long as the structures and components are not within the soybean genome. Similarly, a nucleotide sequence encoding a *Primula juliae* delta 6 desaturase protein or *Neurospora crassa* delta 15 desaturase protein would be an isolated nucleotide sequence so long as the nucleotide sequence was not within the DNA of the organism (*P. juliae* or *N. crassa*) from which the structure was first observed. An artificial nucleotide sequence encoding the same amino acid sequence or a substantially identical amino acid sequence that the native *N. crassa* nucleotide sequence encodes would be considered to be isolated for the purposes of this disclosure. For the purposes of this disclosure, any transgenic nucleotide sequence, i.e., the nucleotide sequence of the DNA inserted into the genome of the cells of the soybean plant event MON87769 would be considered to be an isolated nucleotide sequence whether it is present within the plasmid used to transform soybean cells from which the MON87769 event arose, within the genome of the event MON87769, present in detectable amounts in tissues, progeny, biological samples or commodity products derived from the event MON87769. The nucleotide sequence or any fragment derived therefrom would therefore be considered to be isolated or isolatable if the DNA molecule can be extracted from cells, or tissues, or homogenate from a plant or seed or plant organ; or can be produced as an amplicon from extracted DNA or RNA from cells, or tissues, or homogenate from a plant or seed or plant organ, any of which is derived from such materials derived from the event MON87769. For that matter, the junction sequences as set forth at SEQ ID NO:1 and SEQ ID NO:2, and nucleotide sequences derived from event MON87769 that also contain these junction sequences are considered to be isolated or isolatable, whether these sequences are present within the genome of the cells of event MON87769 or present in detectable amounts in tissues, progeny, biological samples or commodity products derived from the event MON87769.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987).

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from soybean event MON87769 whether from a soybean plant or from a sample that includes DNA from the event. Probes according to the present invention include not only deoxyribonucleic or ribonucleic acids but also polyamides and other probe materials that bind specifically to a target DNA sequence and such binding can be used to detect the presence of that target DNA sequence.

"Primers" are isolated nucleic acids that are annealed to a complementary target DNA strand by nucleic acid hybridization to form a hybrid between the primer and the target DNA strand, and then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 11 nucleotides or more in length, preferably 18 nucleotides or more, more preferably 24 nucleotides or more, and most preferably 30 nucleotides or more. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods. One or more primers, primer pairs, or probes, for instance comprising at least 11 contiguous nucleotides of any one or more of SEQ ID NOs: 1-6 or the complements thereof, may be "derived" from SEQ ID NOs:1-6 of the present invention by nucleotide synthesis, cloning, amplification, or other standard methods for producing a molecule comprising a polynucleotide. Likewise, one or more nucleotide sequences to be derived from any of SEQ ID NOs:1-6, or a complementary sequence thereto, may chosen, for instance, via in silico analysis, as is well known (e.g. Wojciech and Rhoads, *NAR* 17:8543-8551, 1989).

Methods for preparing and using probes and primers are described, for example, in *Molecular Cloning: A Laboratory Manual*, 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a nucleic acid of the present invention will specifically hybridize to one or more of the nucleic acid molecules set forth in SEQ ID NO: 1 and 2 or complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO:1 and SEQ ID NO: 2 or complements or fragments of either under high stringency conditions. In one aspect of the present invention, a preferred marker nucleic acid molecule of the present invention has the nucleic acid sequence set forth in SEQ ID NO: 1 and SEQ ID NO: 2 or complements thereof or fragments of either. In another aspect of the present invention, a preferred marker nucleic acid molecule of the present invention shares 80%, 81%, 82%, 83%, 84%, 85%, 86%, 87%, 88%, 89%, 90%, 912%, 92%, 93%, 94$, 95%, 96%, 97%, 98%, 99% and 100% sequence identity with the nucleic acid sequence set forth in SEQ ID NO: 1 and SEQ ID NO: 2 or complement thereof or fragments of either. In a further aspect of the present invention, a preferred marker nucleic acid molecule of the present invention shares 95% 96%, 97%, 98%, 99% and 100% sequence identity with the sequence set forth in SEQ ID NO: 1 and SEQ ID NO: 2 or complement thereof or fragments of either. SEQ ID NO: 1 and SEQ ID NO: 2 may be used as markers in plant breeding methods to identify the progeny of genetic crosses similar to the methods described for simple sequence repeat DNA marker analysis, in "DNA markers: Protocols, applications, and overviews", pp. 173-185, in Cregan, et al., eds., Wiley-Liss NY, 1997; all of which is herein incorporated by reference. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains transgenic event genomic DNA from the soybean plant of the present invention, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, preferably plus about fifty nucleotide base pairs, more preferably plus about two hundred-fifty nucleotide base pairs, and even more preferably plus about four hundred-fifty nucleotide base pairs. Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA molecule, this distance can range from one nucleotide base pair up to about twenty thousand nucleotide base pairs. The use of the term "amplicon" specifically excludes primer-dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking sequence from a plant or seed tissue comprising soybean event MON87769 can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. One such method is Genetic Bit Analysis (e.g. Nikiforov, et al. *Nucleic Acid Res.* 22:4167-4175, 1994) where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (*Innov. Pharma. Tech.* 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen, et al., (*Genome Res.* 9:492-498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TaqMan® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (*Nature Biotech.* 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties that results in the production of a fluorescent signal. The fluorescent signal indicates the presence of the flanking/transgene insert sequence due to successful amplification and hybridization.

Other described methods, such as microfluidics (US Patent Pub. 2006068398, U.S. Pat. No. 6,544,734) provide methods and devices to separate and amplify DNA samples. Optical dyes are used to detect and quantitate specific DNA molecules (WO/05017181). Nanotube devices (WO/06024023) that comprise an electronic sensor for the detection of DNA molecules or nanobeads that bind specific DNA molecules and can then be detected.

DNA detection kits can be developed using the compositions disclosed herein and the methods well known in the art of DNA detection. The kits are useful for the identification of soybean event MON87769 DNA in a sample and can be applied to methods for breeding soybean plants containing the appropriate event DNA. The kits may contain DNA primers or probes that are homologous or complementary to SEQ ID NO: 1 through SEQ ID NO: 5 or DNA primers or probes homologous or complementary to DNA contained in the transgene genetic elements of DNA. These DNA sequences can be used in DNA amplification reactions or as probes in a DNA hybridization method. The sequences of the genomic DNA and transgene genetic elements contained in a soybean genome comprising event MON87769 consist of a two-gene cassette organized as follows: the nopaline right border sequence, followed by the first gene cassette comprised of the promoter and leader sequence from the *Glycine max* 7S alpha' subunit of the beta-conglycinin storage protein (alpha'-bcsp) gene, which is upstream of the *Primula juliae* delta 6 desaturase (WO2005021761, incorporated by reference), which is upstream of the 3' UTR of the tml (tumor morphology large) gene from *Agrobacterium* octopine-type Ti plasmid, followed by the second gene cassette which is comprised of the promoter and leader sequence from the *Glycine max* 7S alpha subunit of beta-conglycinin gene, which is upstream of the codon-optimized *Neurospora crassa* delta 15 desaturase (US20060156435, incorporated by reference), which is upstream of the 3' UTR of the pea RbcS2 gene, followed by the octopine left border sequence (e.g. FIG. 1). DNA molecules useful as primers in DNA amplification methods can be derived from the sequences of the genetic elements of the transgene insert contained in the MON87769 event. These primer molecules can be used as part of a primer set that also includes a DNA primer molecule derived from the genome flanking the transgene insert of event MON87769 as presented in SEQ ID NO: 3 from bases 1 through 988 and SEQ ID NO: 4 from bases 1 through 939.

The soybean plant MON87769 was produced by an *Agrobacterium* mediated transformation process of an inbred soybean line with the plasmid construct pMON77245 (as shown in FIG. 1). The transformation method used is similar to that described in U.S. Pat. No. 5,914,451. The plasmid construct pMON77245 contains the linked plant expression cassettes with the regulatory genetic elements necessary for expression of the desaturase proteins in soybean plant cells. Soybean cells were regenerated into intact soybean plants and individual plants were selected from the population of plants that showed integrity of the plant expression cassettes and an oil composition comprising SDA as well as a loss of the unlinked glyphosate resistance selection cassette. A soybean plant that contains in its genome the linked plant expression cassettes of pMON77245 is an aspect of the present invention.

The plasmid DNA inserted into the genome of a soybean plant comprising the event designated as MON87769 was characterized by detailed molecular analyses. These analyses included: the insert number (number of integration sites within the soybean genome), the copy number (the number of copies of the T-DNA within one locus), and the integrity of the inserted gene cassettes. DNA molecular probes were used that included the intact desaturase coding regions and their respective regulatory elements, the promoters, introns, and polyadenylation sequences of the plant expression cassettes, and the plasmid pMON77245 backbone DNA region. The data show that a soybean genome comprising event MON87769 contains a single T-DNA insertion with one copy of the desaturase cassette. No additional elements from the transformation vector pMON77245, linked or unlinked to intact gene cassettes, were detected in the genome of MON87769. Finally, inverse PCR and DNA sequence analyses were performed to determine the 5' and 3' insert-to-plant genome junctions, confirm the organization of the elements within the insert (FIG. 2), and determine the complete DNA sequence of the insert in a soybean plant comprising event MON87769 (SEQ ID NO:5).

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

DEPOSIT INFORMATION

A deposit was made of at least 2500 seeds of seed line MON87769, comprising the transgenic soybean event designated MON87769. The deposit was made with the American Type Culture Collection (ATCC), 10801 University Boulevard, Manassas, Va. 20110-2209, USA. The deposit is assigned ATCC Accession No. PTA-8911. The date of deposit was Feb. 5, 2008. Access to the deposit will be available during the pendency of the application to persons entitled thereto upon request. The deposit will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

EXAMPLES

Example 1

Transformation of Soybean A3525 with pMON77245 and Event Selection

The initial transgenic soybean plant comprising the event designated as MON87769 was generated by an *Agrobacte-* rium-mediated transformation of soybean cells with a DNA fragment derived from pMON77245 (FIG. 1; see U.S. Patent Application Publication No. 20080063691, incorporated by reference). The binary plant transformation vector pMON77245 contains two plant transformation cassettes or T-DNAs. Each cassette is flanked by right border and left border sequences at the 5' and 3' ends of the transformation cassette, respectively. An expression cassette (SEQ ID NO: 7) is used for the expression of two desaturase genes. The two-gene cassette is organized as follows: the nopaline right border sequence, followed by the first gene cassette comprised of the promoter and leader sequence from the *Glycine max* 7S alpha' subunit of the beta-conglycinin storage protein (alpha'-bcsp) gene, which is upstream of the *Primula juliae* delta 6 desaturase (WO2005021761, incorporated by reference), which is upstream of the 3' UTR of the tml (tumor morphology large) gene from *Agrobacterium* octopine-type Ti plasmid, followed by the second gene cassette which is comprised of the promoter and leader sequence from the *Glycine max* 7S alpha subunit of the beta-conglycinin gene, which is upstream of the codon-optimized *Neurospora crassa* delta 15 desaturase (U.S. Patent Applic. Publication 20060156435, incorporated by reference), which is upstream of the 3' UTR of the pea RbcS2 gene, followed by the octopine left border sequence (e.g. FIG. 1). The second transformation cassette contains the gene conferring glyphosate resistance used as the transformation selectable marker.

Explants transformed with pMON77245 were obtained via *Agrobacterium tumefaciens*-mediated transformation. Plants were regenerated from transformed tissue. Developing roots were sampled and assayed by PCR for the presence of the desaturase cassette using primers based upon the desaturase cassette sequence (SEQ ID NO: 7). Approximately 38 R0 transformation events were produced and tested for the presence of a single-copy of the desaturase cassette by Invader® (Third Wave Technologies, Inc., Madison, Wis.). In addition, linkage Southern blot analysis was used to determine the number of transgenic loci in each event. The restriction enzyme SwaI was selected for the locus Southern because it is not contained within the desaturase cassette. This enzyme cleaves with sufficient frequency in the soybean genome as to usually disassociate closely-linked copies of the transgene in multiple copy events. R0 events demonstrating a single-copy insertion of the desaturase cassette were self pollinated to generate R1 seed. The fatty acid composition of the R1 seed was determined by FAME-GC analysis. Values ranged from 8-12% SDA in mature seed. Based on these analyses, 10 events were selected to carry forward.

Southern analysis was performed on the ten selected R2 plants to confirm the presence of the expression cassette and absence of undesired nucleotide sequences from the transformation vector. Additionally the sequences flanking the desaturase cassette insertion site for each event were determined. One progeny line, comprising the event designated as MON87769, was selected based upon its performance characteristics and molecular characterization.

Example 2

Isolation of Flanking Sequences Using Inverse PCR

Sequences flanking the T-DNA insertion in MON87769 were determined using inverse PCR as described in Ochman et al., 1990 (PCR Protocols: A guide to Methods and Applications, Academic Press, Inc.) and by TAIL (Thermal Asymmetric InterLaced) PCR. Plant genomic DNA was isolated from both wild type A3525 and the transgenic line from tissue grown under green house conditions. Frozen leaf tissue was ground by mortar and pestle with liquid nitrogen or mechanical grinding. A volume of 22 mL of extraction buffer was added to ~1 g of ground leaf tissue and incubated at 65° C. for 1 hour. The CTAB extraction buffer consisted of 1.4M NaCl, 2% CTAB, 20 mM EDTA, and 100 mM Tris-HCl pH 8.0. Just prior to use, 0.02% beta-mercaptoethanol and 0.5 mg RNase A was added to the extraction buffer. The samples were extracted with 12 mL of phenol/chloroform/isoamyl alcohol (25:24:1) solution and then centrifuged at 4000×G for 10 minutes at 4° C. The supernatant was transferred to a new tube and the DNA was precipitated with 15 mL of isopropanol. After centrifugation at 4000×G for 10 minutes, the pellets were washed with 5 mL 70% ethanol. A final centrifugation at 4000×G for 5 minutes was performed; the pellets were air dried and then re-suspended in 3004, of water.

An aliquot of DNA was subjected to TAIL PCR and a region of sequence adjacent to the insertion site was isolated and sequenced. Additionally an aliquot of DNA was digested with restriction endonucleases selected based upon restriction analysis of the T-DNA. After self-ligation of restriction fragments, PCR was performed using primers designed from the T-DNA sequence that would amplify sequences extending away from the 5' and 3' ends of the T-DNA. PCR products were separated by agarose gel electrophoresis and purified using a QIAGEN gel purification kit (Qiagen, Valencia, Calif.). The subsequent products were sequenced directly using standard sequencing protocols. Using these two methods, the 5' flanking sequence which extends into the right border sequence of the desaturase cassette T-DNA is presented as SEQ ID NO: 3 ([C], see FIG. 2). The 3' flanking sequence which extends into the left border sequence of the desaturase cassette T-DNA is presented as SEQ ID NO: 4 ([D], see FIG. 2). The portion of the desaturase cassette DNA (SEQ ID NO: 7) from pMON77245 that was fully integrated into the A3525 genomic DNA is presented as SEQ ID NO: 5 ([E], see FIG. 2).

Isolated sequences were compared to the T-DNA sequence to identify the flanking sequence and the co-isolated T-DNA fragment. Confirmation of the presence of the expression cassette was achieved by PCR with primers designed based upon the deduced flanking sequence data and the known T-DNA sequence. The A3525 wild type sequence corresponding to the same region in which the T-DNA was integrated in the transformed line was isolated using primers designed from the flanking sequences in MON87769. The flanking sequences in MON87769 and the A3525 wild type sequence were analyzed against multiple nucleotide and protein databases. This information was used to examine the relationship of the transgene to the plant genome and to look at the insertion site integrity. The flanking sequence and wild type sequences were used to design primers for TaqMan endpoint assays used to identify the events and determine zygosity as described in Example 3.

Example 3

Event-Specific Endpoint TaqMan and Zygosity Assays

Methods used to identify the presence of event MON87769 in a sample are described in an event-specific endpoint TaqMan PCR assay, for which examples of conditions are described in Table 1 and in Table 2. The DNA primers used in the endpoint assay are primers SQ5923 (SEQ ID NO: 8), SQ5924 (SEQ ID NO: 9) and 6FAM™ labeled primer PB2511 (SEQ ID NO: 10). 6FAM™ is a fluorescent dye product of Applied Biosystems (Foster City, Calif.) attached to the DNA primer. For TaqMan MGB (Minor Groove Binding) probes, the 5'exonuclease activity of Taq DNA polymerase cleaves the probe from the 5'-end, between the fluorophore and quencher. When hybridized to the target DNA strand, quencher and fluorophore are separated enough to produce a fluorescent signal.

SQ5923 (SEQ ID NO: 8) and SQ5924 (SEQ ID NO: 9) when used as described with PB2511 (SEQ ID NO: 10) produce a DNA amplicon that is diagnostic for event MON87769 DNA. The controls for this analysis should include a positive control from soybean known to contain event MON87769 DNA, a negative control from non-transgenic soybean and a negative control that contains no template DNA.

These assays are optimized for use with an Applied Biosystems GeneAmp®PCR System 9700, Stratagene Robocycler®, MJ Engine, Perkin-Elmer 9700 or Eppendorf Mastercycler® Gradient thermocycler. Other methods and apparatus may be known to those skilled in the art to produce amplicons that identify the event MON87769 DNA.

DNA amplification in a Stratagene Robocycler, MJ Engine, Perkin-Elmer 9700, Eppendorf Mastercycler Gradient thermocycler, Applied Biosystems GeneAmp PCR System 9700 or MJ Research DNA Engine PTC-225 thermal cycler is performed using the following cycling parameters. When running the PCR in the Eppendorf Mastercycler Gradient or MJ Engine, the thermocycler should be run in the calculated mode. When running the PCR in the Perkin-Elmer 9700, the thermocycler is run with the ramp speed set at maximum.

TABLE 1

Soybean MON87769 Event Specific Endpoint TaqMan PCR

| Step | Reagent | Volume | Comments |
|---|---|---|---|
| 1 | 18 megohm water | adjust for final volume of 10 µl | |
| 2 | 2X Universal Master Mix (Contains dNTPs, enzyme and buffer) | 5.0 µl | 1X final concentration of dNTPs, enzyme and buffer |
| 3 | Primer-1 and Primer-2 Mix (resuspended in 18 megohm water to a concentration of 20 uM for each primer) Example: In a microcentrifuge tube, the following should be added to achieve 500 ul at a final concentration of 20 uM: 100 ul of Primer SQ5923 at a concentration of 100 uM 100 ul of Primer SQ1136 at a concentration of 100 uM 300 ul of 18 megohm water | 0.5 µl | 1.0 µM final concentration |
| 4 | Event 6-FAM ™ MGB Probe PB2511 (resuspended in 18 megohm water to a concentration of 10 uM) | 0.2 µl | 0.2 µM final concentration |
| 5 | Extracted DNA (template): 1. Leaf samples to be analyzed 2. Negative control (non-transgenic DNA) 3. Negative water control (no template control) 4. Positive control (MON87769 DNA) | 3.0 µl | |

TABLE 2

Endpoint TaqMan thermocycler conditions

| Cycle No. | Settings | |
|---|---|---|
| 1 | 50° C. | 2 minutes |
| 1 | 95° C. | 10 minutes |
| 10 | 95° C. | 15 seconds |
| | 64° C. | 1 minute |
| | −1° C./cycle | |
| 30 | 95° C. | 15 seconds |
| | 54° C. | 1 minute |
| 1 | 10° C. | Forever |

Determining zygosity for tissues comprising event MON87769 in a sample was done using an event-specific zygosity endpoint TaqMan PCR for which examples of conditions are described in Table 3 and Table 4. The DNA primers used in the zygosity assay are primers SQ5923 (SEQ ID NO: 8), SQ5924 (SEQ ID NO: 9), SQ5925 (SEQ ID NO: 11), 6FAM™ labeled primer PB2511 (SEQ ID NO: 10) and VIC™ labeled primer PB2512 (SEQ ID NO: 12). 6FAM™ and VIC™ are fluorescent dye products of Applied Biosystems (Foster City, Calif.) attached to the DNA primers.

SQ5923 (SEQ ID NO: 8) and SQ5924 (SEQ ID NO: 9) when used in these reaction methods with PB2511 (SEQ ID NO: 10) produce a DNA amplicon that is diagnostic for event MON87769 DNA. The controls for this analysis should include a positive control from soybean containing event MON87769 DNA, a negative control from non-transgenic soybean and a negative control that contains no template DNA.

SQ5923 (SEQ ID NO: 8) and SQ5925 (SEQ ID NO: 11) when used in these reaction methods with PB2512 (SEQ ID NO: 12) produce a DNA amplicon that is diagnostic for the wild type allele.

Heterozygosity is determined by the presence of both amplicons demonstrated by the liberation of fluorescent signal from both probes PB2511 and PB2512.

These assays are optimized for use with an Applied Biosystems GeneAmp PCR System 9700, Stratagene Robocycler, MJ Engine, Perkin-Elmer 9700 or Eppendorf Mastercycler Gradient thermocycler. Other methods and apparatus known to those skilled in the art that produce amplicons that identify the event MON87769 DNA is within the skill of the art.

DNA amplification in a Stratagene Robocycler, MJ Engine, Perkin-Elmer 9700, Eppendorf Mastercycler Gradient thermocycler, Applied Biosystems GeneAmp PCR System 9700 or MJ Research DNA Engine PTC-225 thermal cycler is performed using the following cycling parameters. When running the PCR in the Eppendorf Mastercycler Gradient or MJ Engine, the thermocycler should be run in the calculated mode. When running the PCR in the Perkin-Elmer 9700, the thermocycler is run with the ramp speed set at maximum.

TABLE 3

Soybean MON87769 Event-Specific Zygosity Endpoint TaqMan PCR

| Step | Reagent | Volume | Comments |
|---|---|---|---|
| 1 | 18 megohm water | adjust for final volume of 10 µl | |

TABLE 3-continued

Soybean MON87769 Event-Specific Zygosity Endpoint TaqMan PCR

| Step | Reagent | Volume | Comments |
|---|---|---|---|
| 2 | 2X Universal Master Mix (Contains dNTPs, enzyme and buffer) | 5.0 μl | 1X final concentration of dNTPs, enzyme and buffer |
| 3 | Zygosity Primer-1, Primer-2, & Primer-3 Mix (resuspended in 18 megohm water to a concentration of 20 uM for each primer) Example: In a microcentrifuge tube, the following should be added to achieve 500 ul at a final concentration of 20 uM: 100 ul of Primer SQ5923 at a concentration of 100 uM 100 ul of Primer SQ5924 at a concentration of 100 uM 100 ul of Primer SQ5925 at a concentration of 100 uM 200 ul of 18 megohm water | 0.5 μl | 1.0 μM final concentration |
| 4 | Event 6-FAM ™ MGB Probe PB2511 (resuspended in 18 megohm water to a concentration of 10 uM) | 0.2 μl | 0.2 μM final concentration |
| 5 | WT VIC ™ MGB Probe PB2512 (resuspended in 18 megohm water to a concentration of 10 uM) | 0.2 μl | 0.2 μM final concentration |
| 6 | Extracted DNA (template): 1. Leaf Samples to be analyzed 2. Negative control (non-transgenic DNA) 3. Negative water control (no template control) 4. Positive control Homozygous MON87769 DNA 5. Positive control Hemizygous MON87769 DNA | 3.0 μl | |

TABLE 4

Zygosity Endpoint TaqMan thermocycler conditions

| Cycle No. | Settings | |
|---|---|---|
| 1 | 50° C. | 2 minutes |
| 1 | 95° C. | 10 minutes |
| 10 | 95° C. | 15 seconds |
|  | 64° C. | 1 minute |
|  | −1° C./cycle | |
| 30 | 95° C. | 15 seconds |
|  | 54° C. | 1 minute |
| 1 | 10° C. | Forever |

Example 4

Identification of Event MON87769 in any MON87769 Breeding Event

The following example describes how one may identify the MON87769 event within progeny of any soybean breeding line comprising event MON87769.

Figure 2:
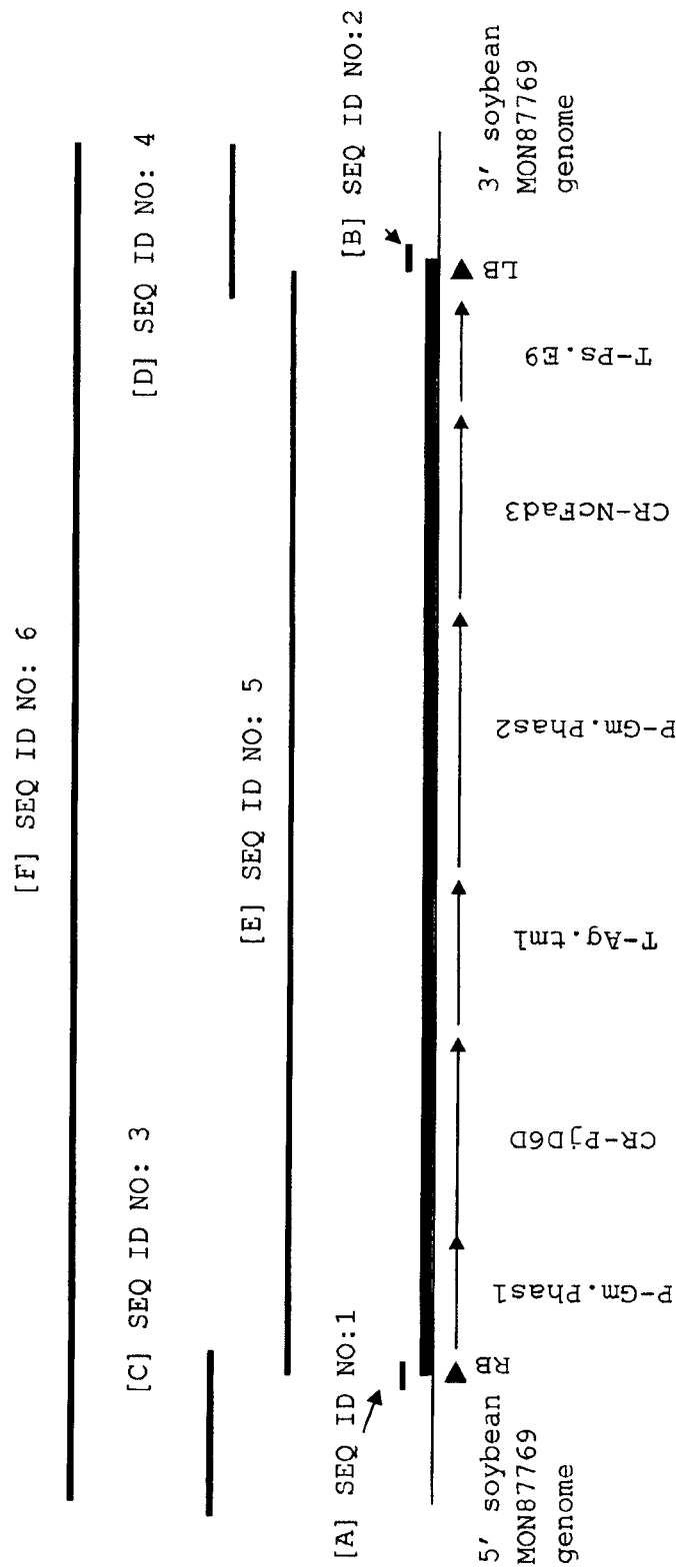
FIG. 2. Organization of the transgenic insert in the genome of a plant comprising soybean event MON87769; [A] corresponds to the relative position of SEQ ID NO: 1 which forms the junction between SEQ ID NO: 3 and SEQ ID NO: 5; [B] corresponds to the relative position of SEQ ID NO: 2 which forms the junction between SEQ ID NO: 4 and SEQ ID NO: 5; [C] corresponds to the relative position of SEQ ID NO: 3, the soybean genome sequence flanking the arbitrarily assigned/designated 5' end of the expression cassette integrated into the genome in event MON87769; [D] corresponds to the relative position of SEQ ID NO: 4, the soybean genome sequence flanking the arbitrarily assigned/designated 3' end of the expression cassette integrated into the genome in event MON87769; [E] represents the various elements comprising SEQ ID NO: 5, the sequence of the expression cassette inserted into the genome of a plant comprising the event MON87769; and [F] represents the contiguous sequence comprising, as represented in the figure from left to right, SEQ ID NO:3, SEQ ID NO:5 and SEQ ID NO:4, in which SEQ ID NO:1 and SEQ ID NO:2 are incorporated as set forth above, as these sequences are present in the genome of a soybean plant comprising event MON87769.

DNA event primer pairs are used to produce an amplicon diagnostic for soybean event MON87769. An amplicon diagnostic for MON87769 comprises at least one junction sequence, SEQ ID NO: 1 or SEQ ID NO: 2 ("[A]" and "[B]", respectively as illustrated in FIG. 2). SEQ ID NO: 1 ([A] of FIG. 2) is a nucleotide sequence corresponding to the junction of the 5' flanking sequence (positions 979 through 988 of SEQ ID NO: 3 [C], see FIG. 2) and the integrated right border of the desaturase cassette (positions 1 through 10 of SEQ ID NO: 5 [E], see FIG. 2). SEQ ID NO: 2 ([B], see FIG. 2) is a nucleotide sequence corresponding to the junction of the integrated left border of the desaturase cassette (positions 7358 through 7367 of SEQ ID NO: 5 [E], see FIG. 2) and the 3' flanking sequence (positions 1 through 10 of SEQ ID NO: 4 [D], see FIG. 2).

Event primer pairs that will produce a diagnostic amplicon for MON87769 include primer pairs based upon the flanking sequences and the inserted desaturase cassette. To acquire a diagnostic amplicon in which at least 11 nucleotides of SEQ ID NO: 1 is found, one would design a forward primer based upon SEQ ID NO: 3 from bases 1 through 978 and a reverse primer based upon the inserted expression desaturase cassette, SEQ ID NO: 5 from positions 10 through 7367. To acquire a diagnostic amplicon in which at least 11 nucleotides of SEQ ID NO: 2 is found, one would design a forward primer based upon the inserted desaturase cassette, SEQ ID NO: 5, from positions 10 through 7357 and a reverse primer based upon the 3' flanking sequence, SEQ ID NO: 4, from bases 10 through 939. For practical purposes, one should design primers which produce amplicons of a limited size range, preferably between 200 to 1000 bases. Smaller sized amplicons in general are more reliably produced in PCR reactions, allow for shorter cycle times and can be easily separated and visualized on agarose gels or adapted for use in endpoint TaqMan™-like assays. In addition, amplicons produced using said primer pairs can be cloned into vectors, propagated, isolated and sequenced or can be sequenced directly with methods well established in the art. Any primer pair derived from the combination of SEQ ID NO: 3 and SEQ ID NO: 5, or one or more subsequence(s) thereof, or the combination of SEQ ID NO: 4 and SEQ ID NO: 5, or one or more subsequence(s) thereof, that are useful in a DNA amplification method to produce an amplicon diagnostic for MON87769 or progeny thereof is an aspect of the present invention. Any single isolated DNA polynucleotide primer molecule comprising at least 11 contiguous nucleotides of SEQ ID NO: 3, or its complement that is useful in a DNA amplification method to produce an amplicon diagnostic for MON87769 or progeny thereof is an aspect of the present invention. Any single isolated DNA polynucleotide primer molecule comprising at least 11 contiguous nucleotides of SEQ ID NO: 4, or its complement that is useful in a DNA amplification method to produce an amplicon diagnostic for MON87769 or progeny thereof is an aspect of the present invention. Any single isolated DNA polynucleotide primer molecule comprising at least 11 contiguous nucleotides of SEQ ID NO: 5, or its complement that is useful in a DNA amplification method to produce an amplicon diagnostic for MON87769 or progeny thereof is an aspect of the present invention.

An example of the amplification conditions for this analysis is illustrated in Table 5 and Table 6. However, any modification of these methods or the use of DNA primers homologous or complementary to SEQ ID NO: 3 or SEQ ID NO: 4 or DNA sequences of the genetic elements contained in the transgene insert (SEQ ID NO: 5) of MON87769 that produce an amplicon diagnostic for MON87769, is within the art. A diagnostic amplicon comprises a DNA molecule homologous or complementary to at least one transgene/genomic junction DNA (SEQ ID NO: 1 or SEQ ID NO: 2), or a substantial portion thereof.

An analysis for event MON87769 plant tissue in a sample should include a positive tissue control from plant tissue comprising event MON87769, a negative control from a soybean plant that does not comprise event MON87769, for example, but not limited to A3525, and a negative control that contains no soybean genomic DNA. A primer pair that will amplify an endogenous soybean DNA molecule will serve as an internal control for the DNA amplification conditions. Additional primer sequences can be selected from SEQ ID NO: 3, SEQ ID NO: 4, or SEQ ID NO: 5 by those skilled in the art of DNA amplification methods, and conditions selected for the production of an amplicon by the methods shown in Table 5 and Table 6 may differ, but result in an amplicon diagnostic for event MON87769 DNA. The use of these DNA primer sequences with modifications to the methods of Table 5 and Table 6 are within the scope of the invention. The amplicon produced by at least one DNA primer sequence derived from SEQ ID NO: 3, SEQ ID NO: 4, or SEQ ID NO: 5 that is diagnostic for MON87769 is an aspect of the invention.

DNA detection kits that contain at least one DNA primer derived from SEQ ID NO: 3, SEQ ID NO: 4, or SEQ ID NO: 5, that when used in a DNA amplification method, produces a diagnostic amplicon for MON87769 or its progeny is an aspect of the invention. A soybean plant or seed, wherein its genome will produce an amplicon diagnostic for MON87769 when tested in a DNA amplification method is an aspect of the invention. The assay for the MON87769 amplicon can be performed by using an Applied Biosystems GeneAmp PCR System 9700, Stratagene Robocycler, MJ Engine, Perkin-Elmer 9700 or Eppendorf Mastercycler Gradient thermocycler or any other amplification system that can be used to produce an amplicon diagnostic of event MON87769 as shown in Table 6.

TABLE 5

Soybean MON87769 Event Specific PCR Assay

| Step | Reagent | Volume | Comments |
|---|---|---|---|
| 1 | 18 megohm water | adjust for final volume of 10 μl | |
| 2 | 2X Universal Master Mix (Contains dNTPs, enzyme and buffer) | 5.0 μl | 1X final concentration of dNTPs, enzyme and buffer |
| 3 | Primer-1 and Primer-2 Mix (resuspended in 18 megohm water to a concentration of 20 μM for each primer) Example: In a microcentrifuge tube, the following should be added to achieve 500 ul at a final concentration of 20 uM: 100 ul of Primer 1 at a concentration of 100 μM 100 ul of Primer 2 at a concentration of 100 μM 300 ul of 18 megohm water | 0.5 μl | 1.0 μM final concentration |
| 5 | Extracted DNA (template) 50 ng of genomic DNA: Leaf samples to be analyzed Negative control (non-transgenic DNA) Negative water control (no template control) Positive control MON88769 DNA | 3.0 μl | |

TABLE 6

Soybean MON87769 Event Thermocycler Conditions

| Cycle No. | Settings | |
|---|---|---|
| 1 | 50° C. | 2 minutes |
| 1 | 95° C. | 10 minutes |
| 10 | 95° C. | 15 seconds |
| | 64° C. | 1 minute −1° C./cycle |
| 30 | 95° C. | 15 seconds |
| | 54° C. | 1 minute |
| 1 | 10° C. | Forever |

Having illustrated and described the principles of the present invention, it should be apparent to persons skilled in the art that the invention can be modified in arrangement and detail without departing from such principles. We claim all modifications that are within the spirit and scope of the appended claims.

The invention claimed is:

1. Oil derived from soybean seed comprising event MON87769 or the progeny thereof, wherein the oil comprises a detectable amount of a DNA molecule comprising SEQ ID NO: 1 or SEQ ID NO: 2 and further comprising a nucleic acid sequence encoding a *Primula juliae* delta 6 desaturase, a representative sample of seed comprising said event MON87769 having been deposited under ATCC Accession No. PTA-8911.

2. A commodity product derived from the oil of claim 1 selected from the group consisting of cooking oil, salad oil, shortening, lecithin, nontoxic plastics, printing inks, lubricants, waxes, hydraulic fluids, electric transformer fluids, solvents, cosmetics, hair care products and biodiesel, wherein the commodity product comprises a detectable amount of a DNA molecule comprising SEQ ID NO: 1 or SEQ ID NO: 2 and further comprising a nucleic acid sequence encoding a *Primula juliae* delta 6 desaturase.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial sequence
<220> FEATURE:
<223> OTHER INFORMATION: 5' Junction Sequence between Glycine max
      genomic DNA and sequence from plasmid pMON77245

<400> SEQUENCE: 1
tgtagattga tcaaacactg                                              20

<210> SEQ ID NO 2
<211> LENGTH: 20
<212> TYPE: DNA
```

<213> ORGANISM: Artificial sequence
<220> FEATURE:
<223> OTHER INFORMATION: 3' Junction Sequence between sequence from plasmid pMON77245 and Glycine max genomic DNA

<400> SEQUENCE: 2
ttacaattga ccatcatact    20

<210> SEQ ID NO 3
<211> LENGTH: 988
<212> TYPE: DNA
<213> ORGANISM: Glycine max

<400> SEQUENCE: 3

```
agataaagtt gactagactc aaactaaagt agttaaaacc aaagggactg agaaagatca    60
atcctgagat agagaaagag aaaggaattt gtaaaacaaa aatcccataa acaactgtca   120
atgttgaaga gcccactctt gatgtgactt agccacataa cgttaatgag ccaattacta   180
ttcctgatgt gcttgctcag aatatggtaa agctgactac taccactatt tctccaactc   240
cttcaagtca atttcaaatt atttaaactt taactcttat gtctaaggtt aaaatttctt   300
caatgtacaa caaattattc tatattttct taggaaagaa aattcctcca agaacacct    360
catatgatag gcgaggtagg ggtttggttc tttgacacca tcaaggtcct ttacgaaggt   420
ttgatcatat gactgtatct catgatctcc cttcattatg gaatattgac ctcaagggat   480
ttgagttcat cacaactaac aaattgctta caaaagttga tgttgagatg atggattatg   540
ttggagtcga taactatttg gatttttattg aggtattcct tctctgatct gctgcttcaa   600
ttctctattg gagaaataga tatgctaaat atgaggcaaa acaaagatg ataatgaatt   660
aaaggaagaa cctaattgtg gccatcaatg aaaagaatat tttggtaact aagaagattg   720
aaatcattaa tagttttcgg caaaaagttg ctaatcatga gaagatggtt ttttccaagg   780
tttttgagaa tgaaaaactg gtcaaggcta tttgatggcc ttaatatgaa actcaacctt   840
gcagttaagg atttagtagg aaccaaaaag attgtcagtg ctttcaatga tcaattgact   900
actagagaag agaagaaaaa gttccttgag ttggaaaggg ataaccttt gaaggagaag    960
aagttggttg aacagcaatg tagattga    988
```

<210> SEQ ID NO 4
<211> LENGTH: 939
<212> TYPE: DNA
<213> ORGANISM: Glycine max

<400> SEQUENCE: 4

```
ccatcatact caaaacttca cgagcaactt gctaattttg gaaagagaa agaaaagaca    60
agtgtcgagc atacacttta gatgcaacaa gccttcataa tgggccatga agatggtttc   120
caaaaagctc tttgccaaat tcaattgctt gcttttgagg tagatttaat gttatttgat   180
tgtttgaaga atgtcaagaa tggggagttg gtaagggagt ctcaaatgga gacttttgaa   240
gaggcttctg gaaatgagac gacctccaag gaagaagata ttgaggcaac ttcaagcctt   300
acactgactt ccaacattcc aactgcataa ttttaattta atgttttttt agaattattt   360
aagtcattgg gccatatgtt ttgtgtattt ttttagtgt tataatatac taaatctcaa   420
tctaatgaaa caagtgttgt gttcatactt gtgttataaa aattgaaaat tttcataagt   480
ataaatttgg ttgtcaagtc taactataat caatagataa cagataaaag taattattga   540
gtactaaaca taagttttaa atgcaagact tactgagttg taaagctata agtattaaac   600
```

```
cgacttctaa tttctataat tattctaact ttcttcttaa aattttttgtt ttctttgtta      660 tgtgccgatg tactggttgt acttagttta aaggtcgtta tgtgtttaca caaagacata      720
caaggtcagt gtactgtttg tactagacat aaataggtca tcgtcaatac atagtttttt     780
gcaagacatt ttttacttg ttctttcatt ttgttcatgt tttctgactt tgtgtaagcat     840 aaataataaa aataagtatt aacaacaata aatggaaaat gagatgaaca gtaaaaggat     900
ttcattaaaa gattataatg ataggaattt cctttttaca                            939

<210> SEQ ID NO 5
<211> LENGTH: 7367
<212> TYPE: DNA
<213> ORGANISM: Artificial sequence
<220> FEATURE:
<223> OTHER INFORMATION: Inserted Cassette from plasmid pMON77245

<400> SEQUENCE: 5
tcaaacactg atagttttaaa ctgaaggcgg gaaacgacaa tctgatcccc atcaagcttg       60
atggccgcgg tacggtcgac tctagaggat ccccggcaaa acatttaat acgtattatt      120 taagaaaaaa atatgtaata atatatttat attttaatat ctattcttat gtattttta      180 aaaatctatt atatattgat caactaaaat attttatat ctacacttat tttgcattt      240 tatcaattt cttgcgtttt ttggcatatt taataatgac tattctttaa taatcaatca      300
ttattcttac atggtacata ttgttggaac catatgaagt gtccattgca tttgactatg      360
tggatagtgt tttgatccag gcctccattt gccgcttatt aattaatttg gtaacagtcc      420
gtactaatca gttacttatc cttcctccat cataattaat cttggtagtc tcgaatgcca      480
caacactgac tagtctcttg gatcataaga aaagccaag gaacaaaaga agacaaaaca      540
caatgagagt atccttttgca tagcaatgtc taagttcata aaattcaaac aaaaacgcaa      600
tcacacacag tggacatcac ttatccacta gctgatcagg atcgccgcgt caagaaaaaa      660
aaactggacc ccaaaagcca tgcacaacaa cacgtactca caaaggtgtc aatcgagcag      720
cccaaaacat tcaccaactc aacccatcat gagcccacac atttgttgtt tctaacccaa      780 cctcaaaactc gtattctctt ccgccaccct atttttgtt atttcaacac ccgtcaaact      840
gcatgccacc ccgtggccaa atgtccatgc atgttaacaa gacctatgac tataaatatc      900
tgcaatctcg gcccaggttt tcatcatcaa gaacccggta ccgagctcga catgactaag      960
accatttaca taaccagctc agaacttgaa aaacataaca agccaggtga cctatggata     1020
tcaattcacg gtcaagttta cgacgtttct tcctgggctg cgcttcaccc gggggggcatc     1080 gctcccctcc tcgcccttgc aggacatgat gtgaccgacg ctttcctcgc ttaccatccc     1140
ccttccacct cccgcctcct ccctcccttc tccaccaacc tacttctaga aaaacattcc     1200
gtgtccgaga cctcttccga ctatcgcaaa cttctagaca gctttcataa gatgggcatg     1260
tttcgtgcca ggggccacac tgcctacgcg acctttgtca ttatgatact tatgttggtt     1320
tcctctgtga ctggggtgct ttgcagtgag aatccgtggg tgcatttggt ttgtggagcg     1380
gcaatggggt ttgcctggat ccagtgcgga tggataggtc atgattccgg acattaccgg     1440
ataatgactg acaggaaatg gaaccggttc gctcagatcc tgagctcaaa ctgcctccaa     1500
gggattagca tcgggtggtg gaagtggaac cacaacgcgc accacattgc ctgcaatagt     1560
ctggagtacg accctgacct ccagtacatt cccttgttgg ttgtgtcccc gaagttcttt     1620 aactcccctca cttctcgttt ctacgacaag aagctgaact tcgacggtgt gtcgaggttt     1680
ttggttcaat accagcactg gtcgttttat ccggtcatgt gtgttgctag gctgaacatg     1740
```

```
cttgcgcagt cgtttatact gcttttttcg aggagggagg tggcgaacag ggtgcaggag    1800
attcttggac tagcggtttt ttggcttggg tttccgctcc tgctttcttg ccttcctaat    1860
tggggtgaga gaataatgtt tttgctcgcg agctactccg ttacgggat acaacacgtg     1920 cagttcagct tgaaccattt ctcatctgac gtttacgtgg gcccacccgt aggtaacgat    1980
tggtttaaga aacagactgc agggacactc aacatatcgt gcccggcgtg gatggattgg   2040
ttccatggcg ggttgcagtt tcaggtcgag caccacttgt tcccgcggat gcctaggggt    2100
cagtttcgga agatttctcc ttttgtgagg gatttgtgta agaaacacaa tttgacttac    2160
aatattgcgt cttttactaa agcaaatgtg ttgacgcttg agaccctgag aaacacagcc    2220
attgaggctc gggacctctc taatccgatc ccaaagaata tggtgtggga ggctgttaaa    2280
aatgtcgggt gaccaattcc cgggggagga aattacactg aggaaggaga agatgacgac    2340
gatgagatgg acgatgaagg ggaggctggt ggagcggaac caagagagtg tcagatcgga    2400
aaccttatca attatccgat cattgcttta gggtcatgcg atctttccgc ataattcccg    2460
tcgccgacac ctaataaagt cggctaatct atgtgattga gtgtgtcttg actttgttat    2520
tttgcatgtt tccaatgtca tttagtaacg aaataaacgt tatcctcttc taaaagcagg    2580
ctgtgttttc ggcaaacatc gccacccatc gctagttttt ctaaaagtgt tctaagctag    2640
cctggtaata atctatacga gcttatattt ctaatcattg ccgaaaaatc ctgtttcgaa    2700
ataattttgt aactctcttt aatatcacca cgatcacaca agaagaagaa ttaaatataa    2760
catttatcag cccacgatga acatggcgaa aattacaagc gaacacaatt gtcttattca    2820
ttaataatta attcaacaaa gttctcagac actccttgat ttaacagaag attttataag    2880
cacctctatg atgcaacaac caaaacgaca tagacttcga aatcccgccc cataaaaact    2940
agatagcacc atctaactcc acgtcttcaa gagcagcctc cgggaggaaa gctgaacagc    3000
ccacagcgat caaagataa tccaatggtt ggcggcgct tggcatttc cttttccaaa      3060 cgtccttgct ttgaccaaaa gtgttccgga cgactcctat gcgttcgaac tcgttgctgg    3120
cctgaattgc tagaaagtac gaggatgaat attcattttt gctgtagttg atccgaccac    3180
cgtctccgct taaggcttgc agttgcgccc tcacctgccg gaatgtataa ccatcagaat    3240
agggttccag gcggccatcg aattcctgca gcccggggga tccactagtt ctagagcggc    3300
cgcgaattca ctagtgatta agcttatgca gggtcgacgg cccgggctgg tctgtctttt    3360 caatttttt ggccacatat tattcgggtt ctgtgacctt tcaaaatga ctgctattac      3420 ctcctgacct tgctattaca tcttgaccat cactaggcat ttaaaagtat tagtcatagt    3480
cacatattac tacaaagcga gattgatctc tctaatctaa tgggtgggaa aacacttata    3540
atatatgatt caagaaaaga aagtaaataa aacaattta ttatataaag actattagga    3600 taaaaaaac cttaaaagtg cttggatttg gaccagactt gaattttaat ttaatgatat    3660
tataatatgt gaatatattt ttgagacaat tgtaaatttc agataaaaa ataatgtaat    3720 taaaattgta ataactatat cgtatactta attaattatt aaatgtgaca aaaaagatat    3780
acatcaaaac ttaatgtttc atgacttttt tttttaatgt gtgtcctaaa tagaaattaa    3840
aaataaaaat tattatatcc aaatgaaaaa aacatttaat acgtattatt taagaaataa    3900
caatatattt atattttaat atgtattcac atgtaaattt aaaaacaaaa acaaatttc    3960 tcttttattg attaattaaa ataatttat aactacattt attttctatt attatcaatt    4020
ttcttctgtt tttttatttg gcatatatac ctagacaagt caaaaaatga ctattcttta   4080
```

```
ataatcaatc attattctta catattgttc gaactacgag ttatgaagtg tcaattgcac      4140
cttagtgttt tgataggcct ccatttgccg ctcattaatt aatttgataa cagccgtacc      4200
gatcaattac ttatgcttct tccatcgtaa ttatatgcat gtcggttctt ttaatcttgg      4260
tactctcgaa tgccaccaca acactgacta gtctcttgga tcatgagaaa aagccaaaga      4320 acaaaaaga caacataaag agtatccttt gcaaaaaaat gtctaagttc ataaaataca       4380
aacaaaaacg caatcacaca cagtggaccc aaaagccatg cacaacaaca cgtactcacc      4440
aaggtgcaat cgtgctgccc aaaaacattc accaactcaa tccatgatga gcccacacat      4500
ttgttgtttg taaccaaatc tcaaacgcgg tgttctcttt ggaaagcaac catatcagca      4560
tatcacacta tctagtctct tggatcatgc atgcgcaacc aaaagacaac acataaagta      4620
tcctttcgaa agcaatgtcc aagtccatca aataaaattg agacaaaatg caacctcacc      4680
ccacttcact atccatggct gatcaagatc gccgcgtcca tgtaggtcta aatgccatgc      4740
acatcaacac gtactcaaca tgcagcccaa attgctcacc atcgctcaac acatttcttg      4800
ttaatttcta agtacactgc ctatgcgact ctaactcgat cacaaccatc ttccgtcaca      4860
tcaattttgt tcaattcaac acccgtcaac ttgcatgcca ccccatgcat gcaagttaac      4920
aagagctata tctcttctat gactataaat acccgcaatc tcggtccagg ttttcatcat      4980
cgagaactag ttcaatatcc tagtatacct taataaataa tttaagatac tagatcgatc      5040
tatcgattct aggacaaaaa tggctgtcac tactaggtca cacaaagccg ccgctgccac      5100
cgaacctgaa gttgtgtcta caggagtgga tgcagtcagc gctgccgcac caagcagtag      5160
tagctcctca tcctcccaaa agtcagctga gcctatcgaa tatccagaca tcaagacaat      5220
tcgtgacgct ataccagacc actgctttag acctcgcgtt tggatatcca tggcgtactt      5280
tattcgcgat tttgcaatgg ctttcggcct cggatacttg gcatggcaat acatcccttt      5340
gattgcaagt accccattga gatacggagc ttgggctttg tacggttacc tccagggact      5400
cgtctgtact ggaatttgga tcttggctca cgaatgcggt cacggagcct tttctagaca      5460
cacctggttc aacaacgtta tgggttggat tggtcactct ttcctactag tcccatattt      5520
tagctggaaa ttttcccatc accgtcatca taggttcacc ggacatatgg aaaaagatat      5580
ggcgttcgtt ccagccacgg aggcggacag aaatcagaga aaactagcta atctctatat      5640
ggacaaagag actgcggaga tgttcgagga tgttcctatt gtgcagttgg ttaaactaat      5700
tgctcaccaa ctcgccggtt ggcagatgta tctcttgttc aacgttagtg ccggaaaagg      5760
ctccaaacag tgggaaaccg gcaaaggtgg aatgggatgg ctccgcgtga gccatttcga      5820
accaagttca gccgttttca gaaacagcga agcaatttac atagctctaa gcgatctcgg      5880
acttatgatt atgggataca ttctctacca ggcagcccaa gttgttggat ggcaaatggt      5940
tggtctcttg tattttcaac agtacttctg ggttcaccat tggctcgttg ccatcactta      6000
ccttcatcac acacacgaag aagttcacca ctttgatgca gattcttgga catttgttaa      6060
gggtgccctc gctaccgtgg acagagactt cggtttcatc ggcaagcacc tcttccataa      6120
catcattgac catcatgttg ttcatcacct cttcccaaga atccctttct actacgctga      6180
agaagctacc aattcaataa gacctatgct cggacctctt taccacagag atgaccgttc      6240
tttcatgggg caactctggt acaacttcac acactgcaaa tgggttgtcc ctgatcctca      6300
agtgccaggt gctctaatct gggctcacac cgttcagagt actcagtaac tgcagtattg      6360
tgtcttcact gactggaaag gagataggat cctctagcta gagctttcgt tcgtatcatc      6420
ggtttcgaca acgttcgtca agttcaatgc atcagtttca ttgcgcacac accagaatcc      6480
```

-continued

```
tactgagttt gagtattatg gcattgggaa aactgttttt cttgtaccat tgttgtgct    6540 tgtaatttac tgtgttttt attcggtttt cgctatcgaa ctgtgaaatg gaaatggatg    6600
gagaagagtt aatgaatgat atggtccttt tgttcattct caaattaata ttatttgttt   6660
tttctcttat ttgttgtgtg ttgaatttga aattataaga gatatgcaaa cattttgttt   6720
tgagtaaaaa tgtgtcaaat cgtggcctct aatgaccgaa gttaatatga ggagtaaaac   6780
acttgtagtt gtaccattat gcttattcac taggcaacaa atatattttc agacctagaa   6840
aagctgcaaa tgttactgaa tacaagtatg tcctcttgtg ttttagacat ttatgaactt   6900
tcctttatgt aatttccag aatccttgtc agattctaat cattgcttta taattatagt    6960
tatactcatg gatttgtagt tgagtatgaa atattttt aatgcatttt atgacttgcc     7020
aattgattga caacatgcat caatcgaccg taccgcggcc gatccccggg cggccgcatc   7080
gatcgtgaag tttctcatct aagcccccat ttggacgtga atgtagacac gtcgaaataa   7140
agatttccga attagaataa tttgtttatt gctttcgcct ataaatacga cggatcgtaa   7200
tttgtcgttt tatcaaaatg tactttcatt ttataataac gctgcggaca tctacatttt   7260
tgaattgaaa aaaattggt aattactctt tctttttctc catattgacc atcatactca    7320
ttgctgatcc atgtagattt cccggacatg aagccattta caattga                 7367
```

<210> SEQ ID NO 6
<211> LENGTH: 9294
<212> TYPE: DNA
<213> ORGANISM: Artificial sequence
<220> FEATURE:
<223> OTHER INFORMATION: Sequence spanning insertion site in event
    MON87769: G. max 5' and 3' flanking regions and inserted DNA from
    plasmid pMON77245

<400> SEQUENCE: 6

```
agataaagtt gactagactc aaactaaagt agttaaaacc aaagggactg agaaagatca     60
atcctgagat agagaaagag aaaggaattt gtaaaacaaa aatcccataa acaactgtca    120
atgttgaaga gcccactctt gatgtgactt agccacataa cgttaatgag ccaattacta    180
ttcctgatgt gcttgctcag aatatggtaa agctgactac taccactatt tctccaactc    240
cttcaagtca atttcaaatt atttaaactt taactcttat gtctaaggtt aaaatttctt    300
caatgtacaa caaattattc tatattttct taggaaagaa aattcctcca aagaacacct    360
catatgatag gcgaggtagg ggtttggttc tttgacacca tcaaggtcct ttacgaaggt    420
ttgatcatat gactgtatct catgatctcc cttcattatg gaatattgac ctcaagggat    480
ttgagttcat cacaactaac aaattgctta caaaagttga tgttgagatg atggattatg    540
ttggagtcga taactatttg gatttttattg aggtattcct tctctgatct gctgcttcaa   600
ttctctattg gagaaataga tatgctaaat atgaggcaaa acaaagatg ataatgaatt     660 aaaggaagaa cctaattgtg gccatcaatg aaaagaatat tttggtaact aagaagattg    720
aaatcattaa tagttttcgg caaaaagttg ctaatcatga gaagatggtt ttttccaagg    780 ttttgagaa tgaaaactg gtcaaggcta tttgatggcc ttaatatgaa actcaacctt      840
gcagttaagg atttagtagg aaccaaaaag attgtcagtg ctttcaatga tcaattgact    900
actagagaag agaagaaaaa gttccttgag ttggaaaggg ataaccttt gaaggagaag     960 aagttggttg aacagcaatg tagattgatc aaacactgat agtttaaact gaaggcggga   1020
aacgacaatc tgatccccat caagcttgat ggccgcggta cggtcgactc tagaggatcc   1080
```

```
ccggcaaaaa catttaatac gtattattta agaaaaaaat atgtaataat atatttatat    1140
tttaatatct attcttatgt atttttttaaa aatctattat atattgatca actaaaatat   1200
ttttatatct acacttattt tgcatttttta tcaattttct tgcgtttttt ggcatatttta  1260
ataatgacta ttctttaata atcaatcatt attcttacat ggtacatatt gttggaacca    1320
tatgaagtgt ccattgcatt tgactatgtg gatagtgttt tgatccaggc ctccatttgc    1380
cgcttattaa ttaatttggt aacagtccgt actaatcagt tacttatcct tcctccatca    1440
taattaatct tggtagtctc gaatgccaca acactgacta gtctcttgga tcataagaaa    1500
aagccaagga acaaaagaag acaaaacaca atgagagtat cctttgcata gcaatgtcta    1560
agttcataaa attcaaacaa aaacgcaatc acacacagtg gacatcactt atccactagc    1620
tgatcaggat cgccgcgtca agaaaaaaaa actggacccc aaaagccatg cacaacaaca    1680
cgtactcaca aaggtgtcaa tcgagcagcc caaaacattc accaactcaa cccatcatga    1740
gcccacacat ttgttgtttc taacccaacc tcaaactcgt attctcttcc gccacctcat    1800
ttttgtttat ttcaacaccc gtcaaactgc atgccacccc gtggccaaat gtccatgcat    1860
gttaacaaga cctatgacta taaatatctg caatctcggc ccaggttttc atcatcaaga    1920
accgggtacc gagctcgaca tgactaagac catttacata accagctcag aacttgaaaa    1980
acataacaag ccaggtgacc tatggatatc aattcacggt caagtttacg acgtttcttc    2040
ctgggctgcg cttcacccgg ggggcatcgc tccctcctc gcccttgcag acatgatgt      2100
gaccgacgct ttcctcgctt accatccccc ttccacctcc cgcctcctcc ctcccttctc    2160
caccaaccta cttctagaaa acattccgt gtccgagacc tcttccgact atcgcaaact     2220
tctagacagc tttcataaga tgggcatgtt tcgtgccagg ggccacactg cctacgcgac    2280
ctttgtcatt atgatactta tgttggtttc ctctgtgact ggggtgcttt gcagtgagaa    2340
tccgtgggtg catttggttt gtggagcggc aatggggttt gcctggatcc agtgcggatg    2400
gataggtcat gattccggac attaccggat aatgactgac aggaaatgga accggttcgc    2460
tcagatcctg agctcaaact gcctccaagg gattagcatc gggtggtgga agtggaacca    2520
caacgcgcac cacattgcct gcaatagtct ggagtacgac cctgacctcc agtacattcc    2580
cttgttggtt gtgtccccga agttctttaa ctccctcact tctcgtttct acgacaagaa    2640
gctgaacttc gacggtgtgt cgaggttttt ggttcaatac cagcactggt cgttttatcc    2700
ggtcatgtgt gttgctaggc tgaacatgct tgcgcagtcg tttatactgc tttttttcgag  2760
gagggaggtg gcgaacaggg tgcaggagat tcttggacta gcggtttttt ggctttggtt   2820
tccgctcctg ctttcttgcc ttcctaattg gggtgagaga ataatgtttt tgctcgcgag    2880
ctactccgtt acgggatac aacacgtgca gttcagcttg aaccatttct catctgacgt     2940
ttacgtgggc ccacccgtag gtaacgattg gtttaagaaa cagactgcag ggacactcaa    3000
catatcgtgc ccggcgtgga tggattggtt ccatggcggg ttgcagtttc aggtcgagca    3060
ccacttgttc ccgcggatgc ctaggggtca gtttcggaag atttctcctt ttgtgaggga    3120
tttgtgtaag aaaacacaatt tgacttacaa tattgcgtct tttactaaag caaatgtgtt    3180
gacgcttgag accctgagaa acacagccat tgaggctcgg gacctctcta atccgatccc    3240
aaagaatatg gtgtgggagg ctgttaaaaa tgtcgggtga ccaattcccg ggggaggaaa    3300
ttacactgag gaaggagaag atgacgacga tgagatggac gatgaagggg aggctggtgg    3360
agcggaacca agagagtgtc agatcggaaa ccttatcaat tatccgatca ttgctttagg    3420
gtcatgcgat cttccgcat aattcccgtc gccgacacct aataaagtcg gctaatctat      3480
```

```
gtgattgagt gtgtcttgac tttgttattt tgcatgtttc caatgtcatt tagtaacgaa    3540
ataaacgtta tcctcttcta aaagcaggct gtgttttcgg caaacatcgc cacccatcgc    3600
tagttttcct aaaagtgttc taagctagcc tggtaataat ctatacgagc ttatatttct    3660
aatcattgcc gaaaaatcct gtttcgaaat aattttgtaa ctctctttaa tatcaccacg    3720
atcacacaag aagaagaatt aaatataaca tttatcagcc cacgatgaac atggcgaaaa    3780
ttacaagcga acacaattgt cttattcatt aataattaat tcaacaaagt tctcagacac    3840
tccttgattt aacagaagat tttataagca cctctatgat gcaacaacca aaacgacata    3900
gacttcgaaa tcccgcccca taaaaactag atagcaccat ctaactccac gtcttcaaga    3960
gcagcctccg ggaggaaagc tgaacagccc acagcgatca aaagataatc caatggttgg    4020
ccggcgcttg gcattttcct tttccaaacg tccttgcttt gaccaaaagt gttccggacg    4080
actcctatgc gttcgaactc gttgctggcc tgaattgcta gaaagtacga ggatgaatat    4140 tcattttgc tgtagttgat ccgaccaccg tctccgctta aggcttgcag ttgcgccctc    4200
acctgccgga atgtataacc atcagaatag ggttccaggc ggccatcgaa ttcctgcagc    4260 ccggggggatc cactagttct agagcggccg cgaattcact agtgattaag cttatgcagg    4320
gtcgacggcc cgggctggtc tgtcttttca atttttttgg ccacatatta ttcgggttct    4380 gtgaccttt caaaatgact gctattacct cctgaccttg ctattacatc ttgaccatca    4440
ctaggcattt aaaagtatta gtcatagtca catattacta caaagcgaga ttgatctctc    4500
taatctaatg ggtgggaaaa cacttataat atatgattca agaaaagaaa gtaaataaaa    4560 caatttatt atataaagac tattaggata aaaaaaacct aaaagtgct tggatttgga    4620 ccagacttga atttaatttt aatgatatta taatatgtga atatattttt gagacaattg    4680
taaatttcag ataaaaaaat aatgtaatta aaattgtaat aactatatcg tatacttaat    4740
taattattaa atgtgacaaa aaagatatac atcaaaactt aatgtttcat gactttttt    4800 tttaatgtgt gtcctaaata gaaattaaaa ataaaaatta ttatatccaa atgaaaaaaa    4860
catttaatac gtattattta agaaataaca atatatttat attttaatat gtattcacat    4920
gtaaatttaa aaacaaaaac aaaatttctc ttttattgat taattaaaat aattttataa    4980
ctacatttat tttctattat tatcaatttt cttctgtttt tttatttggc atatatacct    5040
agacaagtca aaaatgact attctttaat aatcaatcat tattcttaca tattgttcga    5100
actacgagtt atgaagtgtc aattgcacct tagtgttttg ataggcctcc atttgccgct    5160
cattaattaa tttgataaca gccgtaccga tcaattactt atgcttcttc catcgtaatt    5220
atatgcatgt cggttctttt aatcttggta ctctcgaatg ccaccacaac actgactagt    5280
ctcttggatc atgagaaaaa gccaaagaac aaaaagaca acataaagag tatcctttgc    5340
aaaaaaatgt ctaagttcat aaaatacaaa caaaaacgca atcacacaca gtggacccaa    5400
aagccatgca caacaacacg tactcaccaa ggtgcaatcg tgctgcccaa aaacattcac    5460
caactcaatc catgatgagc ccacacattt gttgtttgta accaaatctc aaacgcggtg    5520 ttctcttttgg aaagcaacca tatcagcata tcacactatc tagtctcttg gatcatgcat    5580
gcgcaaccaa aagacaacac ataaagtatc ctttcgaaag caatgtccaa gtccatcaaa    5640
taaaattgag acaaaatgca acctcacccc acttcactat ccatggctga tcaagatcgc    5700
cgcgtccatg taggtctaaa tgccatgcac atcaacacgt actcaacatg cagcccaaat    5760
tgctcaccat cgctcaacac atttcttgtt aatttctaag tacactgcct atgcgactct    5820
```

```
aactcgatca caaccatctt ccgtcacatc aattttgttc aattcaacac ccgtcaactt      5880
gcatgccacc ccatgcatgc aagttaacaa gagctatatc tcttctatga ctataaatac      5940
ccgcaatctc ggtccaggtt ttcatcatcg agaactagtt caatatccta gtataccttt      6000
ataaataatt taagatacta gatcgatcta tcgattctag gacaaaaatg gctgtcacta      6060
ctaggtcaca caaagccgcc gctgccaccg aacctgaagt tgtgtctaca ggagtggatg      6120
cagtcagcgc tgccgcacca agcagtagta gctcctcatc ctcccaaaag tcagctgagc      6180
ctatcgaata tccagacatc aagacaattc gtgacgctat accagaccac tgctttagac      6240
ctcgcgtttg gatatccatg gcgtacttta ttcgcgattt tgcaatggct ttcggcctcg      6300
gatacttggc atggcaatac atcccctttga ttgcaagtac cccattgaga tacggagctt      6360
gggctttgta cggttacctc cagggactcg tctgtactgg aatttggatc ttggctcacg      6420
aatgcggtca cggagccttt tctagacaca cctggttcaa caacgttatg ggttggattg      6480
gtcactcttt cctactagtc ccatatttta gctggaaatt ttcccatcac cgtcatcata      6540
ggttcaccgg acatatggaa aaagatatgg cgttcgttcc agccacggag gcggacagaa      6600
atcagagaaa actagctaat ctctatatgg acaaagagac tgcggagatg ttcgaggatg      6660
ttcctattgt gcagttggtt aaactaattg ctcaccaact cgccggttgg cagatgtatc      6720
tcttgttcaa cgttagtgcc ggaaaaggct ccaaacagtg ggaaaccggc aaaggtggaa      6780
tgggatggct ccgcgtgagc catttcgaac caagttcagc cgttttcaga aacagcgaag      6840
caatttacat agctctaagc gatctcggac ttatgattat gggatacatt ctctaccagg      6900
cagcccaagt tgttggatgg caaatggttg gtctcttgta ttttcaacag tacttctggg      6960
ttcaccattg gctcgttgcc atcacttacc ttcatcacac acacgaagaa gttcaccact      7020
ttgatgcaga ttcttggaca tttgttaagg gtgccctcgc taccgtggac agagacttcg      7080
gtttcatcgg caagcacctc ttccataaca tcattgacca tcatgttgtt catcacctct      7140
tcccaagaat cccttttctac tacgctgaag aagctaccaa ttcaataaga cctatgctcg      7200
gacctcttta ccacagagat gaccgttctt tcatggggca actctggtac aacttcacac      7260
actgcaaatg ggttgtccct gatcctcaag tgccaggtgc tctaatctgg gctcacaccg      7320
ttcagagtac tcagtaactg cagtattgtg tcttcactga ctggaaagga gataggatcc      7380
tctagctaga gctttcgttc gtatcatcgg tttcgacaac gttcgtcaag ttcaatgcat      7440
cagtttcatt gcgcacacac cagaatccta ctgagtttga gtattatggc attgggaaaa      7500 ctgttttttct tgtaccattt gttgtgcttg taatttactg tgttttttat tcggttttcg      7560
ctatcgaact gtgaaatgga aatggatgga gaagagttaa tgaatgatat ggtccttttg      7620
ttcattctca aattaatatt atttgttttt tctcttattt gttgtgtgtt gaatttgaaa      7680
ttataagaga tatgcaaaca ttttgttttg agtaaaaatg tgtcaaatcg tggcctctaa      7740
tgaccgaagt taatatgagg agtaaaaacac ttgtagttgt accattatgc ttattcacta      7800
ggcaacaaat atattttcag acctagaaaa gctgcaaatg ttactgaata caagtatgtc      7860
ctcttgtgtt ttagacattt atgaactttc ctttatgtaa ttttccagaa tccttgtcag      7920
attctaatca ttgctttata attatagtta tactcatgga tttgtagttg agtatgaaaa      7980 tatttttttaa tgcattttat gacttgccaa ttgattgaca acatgcatca atcgaccgta      8040
ccgcggccga tccccgggcg gccgcatcga tcgtgaagtt tctcatctaa gccccccattt      8100 ggacgtgaat gtagacacgt cgaaataaag atttccgaat tagaataatt tgtttattgc      8160
tttcgcctat aaatacgacg gatcgtaatt tgtcgtttta tcaaaatgta ctttcatttt      8220
```

```
ataataacgc tgcggacatc tacattttg aattgaaaaa aaattggtaa ttactctttc    8280
ttttctccca tattgaccat catactcatt gctgatccat gtagatttcc cggacatgaa    8340
gccatttaca attgaccatc atactcaaaa cttcacgagc aacttgctaa ttttggaaaa    8400
gagaaagaaa agacaagtgt cgagcataca ctttagatgc aacaagcctt cataatgggc    8460
catgaagatg gtttccaaaa agctctttgc caaattcaat tgcttgcttt tgaggtagat    8520
ttaatgttat ttgattgttt gaagaatgtc aagaatgggg agttggtaag ggagtctcaa    8580
atggagactt ttgaagaggc ttctggaaat gagacgacct ccaaggaaga agatattgag    8640
gcaacttcaa gccttacact gacttccaac attccaactg cataatttta atttaatgtt    8700
tttttagaat tatttaagtc attgggccat atgttttgtg tatttttttt agtgttataa    8760
tatactaaat ctcaatctaa tgaaacaagt gttgtgttca tacttgtgtt ataaaaattg    8820
aaaattttca taagtataaa tttggttgtc aagtctaact ataatcaata gataacagat    8880
aaaagtaatt attgagtact aaacataagt tttaaatgca agacttactg agttgtaaag    8940
ctataagtat taaaccgact tctaatttct ataattattc taactttctt cttaaaattt    9000
ttgttttctt tgttatgtgc cgatgtactg gttgtactta gtttaaaggt cgttatgtgt    9060
ttacacaaag acatacaagg tcagtgtact gtttgtacta gacataaata ggtcatcgtc    9120
aatacatagt tttttgcaag acatttttt acttgttctt tcattttgtt catgtttct    9180 gacttgtgta agcataaata ataaaaataa gtattaacaa caataaatgg aaaatgagat    9240
gaacagtaaa aggatttcat taaaagatta taatgatagg aatttccttt taca           9294

<210> SEQ ID NO 7
<211> LENGTH: 7849
<212> TYPE: DNA
<213> ORGANISM: Artificial Sequence
<220> FEATURE:
<223> OTHER INFORMATION: Expression cassette with Primula juliae and
      Neurospora crassa desaturase genes of pMON77245

<400> SEQUENCE: 7 aggattttc ggcgctgcgc tacgtccgcg accgcgttga gggatcaagc cacagcagcc       60
cactcgacct tctagccgac ccagacgagc caagggatct ttttggaatg ctgctccgtc     120
gtcaggcttt ccgacgtttg ggtggttgaa cagaagtcat tatcgcacgg aatgccaagc    180
actcccgagg ggaaccctgt ggttggcatg cacatacaaa tggacgaacg gataaacctt    240 ttcacgcct tttaaatatc cgattattct aataaacgct cttttctctt aggtttaccc    300
gccaatatat cctgtcaaac actgatagtt taaactgaag gcgggaaacg acaatctgat    360
ccccatcaag cttgatggcc gcggtacggt cgactctaga ggatccccgg caaaaacatt    420
taatacgtat tatttaagaa aaaatatgt aataatatat ttatatttta atatctattc     480
ttatgtattt tttaaaaatc tattatatat tgatcaacta aaatattttt atatctacac    540
ttattttgca tttttatcaa ttttcttgcg ttttttggca tatttaataa tgactattct    600
ttaataatca atcattattc ttacatggta catattgttg gaaccatatg aagtgtccat    660
tgcatttgac tatgtggata gtgttttgat ccaggcctcc atttgccgct tattaattaa    720
tttggtaaca gtccgtacta atcagttact tatccttcct ccatcataat taatcttggt    780
agtctcgaat gccacaacac tgactagtct cttggatcat aagaaaaagc caaggaacaa    840
aagaagacaa aacacaatga gagtatcctt tgcatagcaa tgtctaagtt cataaaattc    900
aaacaaaaac gcaatcacac acagtggaca tcacttatcc actagctgat caggatcgcc    960
```

```
gcgtcaagaa aaaaaaactg gaccccaaaa gccatgcaca acaacacgta ctcacaaagg    1020
tgtcaatcga gcagcccaaa acattcacca actcaaccca tcatgagccc acacatttgt    1080
tgtttctaac ccaacctcaa actcgtattc tcttccgcca cctcattttt gtttatttca    1140
acacccgtca aactgcatgc caccccgtgg ccaaatgtcc atgcatgtta acaagaccta    1200
tgactataaa tatctgcaat ctcggcccag ttttcatca tcaagaaccg ggtaccgagc     1260
tcgacatgac taagaccatt tacataacca gctcagaact tgaaaaacat aacaagccag    1320
gtgacctatg gatatcaatt cacggtcaag tttacgacgt ttcttcctgg gctgcgcttc    1380
acccgggggg catcgctccc ctcctcgccc ttgcaggaca tgatgtgacc gacgctttcc    1440
tcgcttacca tccccttcc acctcccgcc tcctccctcc cttctccacc aacctacttc      1500
tagaaaaaca ttccgtgtcc gagacctctt ccgactatcg caaacttcta gacagctttc    1560
ataagatggg catgtttcgt gccaggggcc acactgccta cgcgaccttt gtcattatga    1620
tacttatgtt ggtttcctct gtgactgggg tgctttgcag tgagaatccg tgggtgcatt    1680
tggtttgtgg agcggcaatg gggtttgcct ggatccagtg cggatggata ggtcatgatt    1740
ccggacatta ccggataatg actgacagga aatggaaccg gttcgctcag atcctgagct    1800
caaactgcct ccaagggatt agcatcgggt ggtggaagtg gaaccacaac gcgcaccaca    1860
ttgcctgcaa tagtctggag tacgaccctg acctccagta cattcccttg ttggttgtgt    1920
ccccgaagtt ctttaactcc ctcacttctc gtttctacga caagaagctg aacttcgacg    1980
gtgtgtcgag gttttggtt caataccagc actggtcgtt ttatccggtc atgtgtgttg      2040
ctaggctgaa catgcttgcg cagtcgttta tactgctttt tcgaggagg gaggtggcga     2100 acagggtgca ggagattctt ggactagcgg ttttttggct ttggtttccg ctcctgcttt    2160
cttgccttcc taattggggt gagagaataa tgttttgct cgcgagctac tccgttacgg     2220
ggatacaaca cgtgcagttc agcttgaacc atttctcatc tgacgtttac gtgggcccac    2280
ccgtaggtaa cgattggttt aagaaacaga ctgcagggac actcaacata tcgtgcccgg    2340
cgtggatgga ttggttccat ggcgggttgc agtttcaggt cgagcaccac ttgttcccgc    2400
ggatgcctag gggtcagttt cggaagattt ctcctttgt gagggatttg tgtaagaaac     2460
acaatttgac ttacaatatt gcgtctttta ctaaagcaaa tgtgttgacg cttgagaccc    2520
tgagaaacac agccattgag gctcgggacc tctctaatcc gatcccaaag aatatggtgt    2580
gggaggctgt taaaaatgtc gggtgaccaa ttcccggggg aggaaattac actgaggaag    2640
gagaagatga cgacgatgag atggacgatg aaggggaggc tggtggagcg gaaccaagag    2700
agtgtcagat cggaaaccct atcaattatc cgatcattgc tttagggtca tgcgatcttt    2760
ccgcataatt cccgtcgccg acacctaata aagtcggcta atctatgtga ttgagtgtgt    2820
cttgactttg ttattttgca tgttttccaat gtcatttagt aacgaaataa acgttatcct    2880
cttctaaaag caggctgtgt tttcggcaaa catcgccacc catcgctagt ttttctaaaa    2940
gtgttctaag ctagcctggt aataatctat acgagcttat atttctaatc attgccgaaa    3000
aatcctgttt cgaaataatt ttgtaactct ctttaatatc accacgatca cacaagaaga    3060
agaattaaat ataacattta tcagcccacg atgaacatgg cgaaaattac aagcgaacac    3120
aattgtctta ttcattaata attaattcaa caaagttctc agacactcct tgatttaaca    3180
gaagatttta taagcacctc tatgatgcaa caaccaaaac gacatagact tcgaaatccc    3240
gccccataaa aactagatag caccatctaa ctccacgtct tcaagagcag cctccgggag    3300
```

```
gaaagctgaa cagcccacag cgatcaaaag ataatccaat ggttggccgg cgcttggcat      3360 tttcctttc  caaacgtcct tgctttgacc aaaagtgttc cggacgactc ctatgcgttc      3420
gaactcgttg ctggcctgaa ttgctagaaa gtacgaggat gaatattcat ttttgctgta      3480
gttgatccga ccaccgtctc cgcttaaggc ttgcagttgc ccctcacct  gccggaatgt      3540 ataaccatca gaatagggtt ccaggcggcc atcgaattcc tgcagcccgg gggatccact      3600
agttctagag cggccgcgaa ttcactagtg attaagctta tgcagggtcg acggcccggg      3660
ctggtctgtc ttttcaattt ttttggccac atattattcg ggttctgtga ccttttcaaa      3720
atgactgcta ttacctcctg accttgctat tacatcttga ccatcactag gcatttaaaa      3780
gtattagtca tagtcacata ttactacaaa gcgagattga tctctctaat ctaatgggtg      3840
ggaaaacact tataatatat gattcaagaa aagaaagtaa ataaaacaat tttattatat      3900
aaagactatt aggataaaaa aaaccttaaa agtgcttgga tttggaccag acttgaattt      3960
taatttaatg atattataat atgtgaatat attttttgaga caattgtaaa tttcagataa      4020
aaaaataatg taattaaaat tgtaataact atatcgtata cttaattaat tattaaatgt      4080
gacaaaaaag atatacatca aaacttaatg tttcatgact tttttttttta atgtgtgtcc      4140 taaatagaaa ttaaaaataa aaattattat atccaaatga aaaaaacatt taatacgtat      4200
tatttaagaa ataacaatat atttatattt taatatgtat tcacatgtaa atttaaaaac      4260
aaaaacaaaa tttctctttt attgattaat taaaataatt ttataactac atttattttc      4320
tattattatc aattttcttc tgtttttta  tttggcatat atacctagac aagtcaaaaa      4380
atgactattc tttaataatc aatcattatt cttacatatt gttcgaacta cgagttatga      4440
agtgtcaatt gcaccttagt gttttgatag gcctccattt gccgctcatt aattaatttg      4500
ataacagccg taccgatcaa ttacttatgc ttcttccatc gtaattatat gcatgtcggt      4560
tcttttaatc ttggtactct cgaatgccac cacaacactg actagtctct tggatcatga      4620 gaaaagcca  agaacaaaa  aagacaacat aaagagtatc ctttgcaaaa aaatgtctaa      4680
gttcataaaa tacaaacaaa aacgcaatca cacacagtgg acccaaaagc catgcacaac      4740
aacacgtact caccaaggtg caatcgtgct gcccaaaaac attcaccaac tcaatccatg      4800
atgagcccac acatttgttg tttgtaacca atctcaaac  gcggtgttct ctttggaaag      4860
caaccatatc agcatatcac actatctagt ctccttggatc atgcatgcgc aaccaaaaga     4920
caacacataa agtatccttt cgaaagcaat gtccaagtcc atcaaataaa attgagacaa      4980
aatgcaacct caccccactt cactatccat ggctgatcaa gatcgccgcg tccatgtagg      5040
tctaaatgcc atgcacatca acacgtactc aacatgcagc ccaaattgct caccatcgct      5100
caacacattt cttgttaatt tctaagtaca ctgcctatgc gactctaact cgatcacaac      5160
catcttccgt cacatcaatt tgttcaatt  caacacccgt caacttgcat gccacccat       5220 gcatgcaagt taacaagagc tatatctctt ctatgactat aaatacccgc aatctcggtc      5280
caggttttca tcatcgagaa ctagttcaat atcctagtat accttaataa ataatttaag      5340
atactagatc gatctatcga ttctaggaca aaaatggctg tcactactag gtcacacaaa      5400
gccgccgctg ccaccgaacc tgaagttgtg tctacaggag tggatgcagt cagcgctgcc      5460
gcaccaagca gtagtagctc ctcatcctcc caaaagtcag ctgagcctat cgaatatcca      5520
gacatcaaga caattcgtga cgctatacca gaccactgct ttagacctcg cgtttggata      5580
tccatggcgt actttattcg cgattttgca atggctttcg gcctcggata cttggcatgg      5640
caatacatcc ctttgattgc aagtaccccca ttgagatacg gagcttgggc tttgtacggt      5700
```

-continued

```
tacctccagg gactcgtctg tactggaatt tggatcttgg ctcacgaatg cggtcacgga    5760
gccttttcta gacacacctg gttcaacaac gttatgggtt ggattggtca ctctttccta    5820
ctagtcccat attttagctg gaaattttcc catcaccgtc atcataggtt caccggacat    5880
atggaaaaag atatggcgtt cgttccagcc acggaggcgg acagaaatca gagaaaacta    5940
gctaatctct atatggacaa agagactgcg gagatgttcg aggatgttcc tattgtgcag    6000
ttggttaaac taattgctca ccaactcgcc ggttggcaga tgtatctctt gttcaacgtt    6060
agtgccggaa aaggctccaa acagtgggaa accggcaaag gtggaatggg atggctccgc    6120
gtgagccatt tcgaaccaag ttcagccgtt ttcagaaaca gcgaagcaat ttacatagct    6180
ctaagcgatc tcggacttat gattatggga tacattctct accaggcagc ccaagttgtt    6240
ggatggcaaa tggttggtct cttgtatttt caacagtact tctgggttca ccattggctc    6300
gttgccatca cttaccttca tcacacacac gaagaagttc accactttga tgcagattct    6360
tggacatttg ttaagggtgc cctcgctacc gtggacagag acttcggttt catcggcaag    6420
cacctcttcc ataacatcat tgaccatcat gttgttcatc acctcttccc aagaatccct    6480
ttctactacg ctgaagaagc taccaattca ataagaccta tgctcggacc tctttaccac    6540
agagatgacc gttctttcat ggggcaactc tggtacaact tcacacactg caaatgggtt    6600
gtccctgatc ctcaagtgcc aggtgctcta atctgggctc acaccgttca gagtactcag    6660
taactgcagt attgtgtctt cactgactgg aaaggagata ggatcctcta gctagagctt    6720
tcgttcgtat catcggtttc gacaacgttc gtcaagttca atgcatcagt ttcattgcgc    6780
acacaccaga atcctactga gtttgagtat tatggcattg ggaaaactgt ttttcttgta    6840
ccatttgttg tgcttgtaat ttactgtgtt tttattcgg ttttcgctat cgaactgtga    6900
aatggaaatg gatggagaag agttaatgaa tgatatggtc cttttgttca ttctcaaatt    6960
aatattattt gttttttctc ttatttgttg tgtgttgaat ttgaaattat aagagatatg    7020
caaacatttt gttttgagta aaaatgtgtc aaatcgtggc ctctaatgac cgaagttaat    7080
atgaggagta aaacacttgt agttgtacca ttatgcttat tcactaggca acaaatatat    7140
tttcagacct agaaaagctg caaatgttac tgaatacaag tatgtcctct gtgtttttag    7200
acatttatga actttccttt atgtaatttt ccagaatcct tgtcagattc taatcattgc    7260
tttataatta tagttatact catggatttg tagttgagta tgaaaatatt ttttaatgca    7320
ttttatgact tgccaattga ttgacaacat gcatcaatcg accgtaccgc ggccgatccc    7380
cgggcggccg catcgatcgt gaagtttctc atctaagccc ccatttggac gtgaatgtag    7440
acacgtcgaa ataaagattt ccgaattaga ataatttgtt tattgctttc gcctataaat    7500
acgacggatc gtaatttgtc gttttatcaa aatgtacttt cattttataa taacgctgcg    7560
gacatctaca tttttgaatt gaaaaaaaat tggtaattac tctttctttt tctccatatt    7620
gaccatcata ctcattgctg atccatgtag atttcccgga catgaagcca tttacaattg    7680
aatatatcct gccgccgctg ccgctttgca cccggtggag cttgcatgtt ggtttctacg    7740
cagaactgag ccggttaggc agataatttc cattgagaac tgagccatgt gcaccttccc    7800
cccaacacgg tgagcgacgg ggcaacggag tgatccacat gggactttt                7849
```

<210> SEQ ID NO 8
<211> LENGTH: 25
<212> TYPE: DNA
<213> ORGANISM: Artificial sequence
<220> FEATURE:

```
<223> OTHER INFORMATION: Synthetic Primer

<400> SEQUENCE: 8
accttttgaa ggagaagaag ttggt                                          25

<210> SEQ ID NO 9
<211> LENGTH: 19
<212> TYPE: DNA
<213> ORGANISM: Artificial sequence
<220> FEATURE:
<223> OTHER INFORMATION: Synthetic Primer

<400> SEQUENCE: 9
tcgtttcccg ccttcagtt                                                 19

<210> SEQ ID NO 10
<211> LENGTH: 20
<212> TYPE: DNA
<213> ORGANISM: Artificial sequence
<220> FEATURE:
<223> OTHER INFORMATION: Synthetic Probe

<400> SEQUENCE: 10
tgatcaaaca ctgatagttt                                                20

<210> SEQ ID NO 11
<211> LENGTH: 24
<212> TYPE: DNA
<213> ORGANISM: Artificial sequence
<220> FEATURE:
<223> OTHER INFORMATION: Synthetic Primer

<400> SEQUENCE: 11
caaaattagc aagttgctcg tgaa                                           24

<210> SEQ ID NO 12
<211> LENGTH: 17
<212> TYPE: DNA
<213> ORGANISM: Artificial sequence
<220> FEATURE:
<223> OTHER INFORMATION: Synthetic Probe

<400> SEQUENCE: 12
agaaggcaac ctcaaaa                                                   17
```